(12) United States Patent
Watanabe et al.

(10) Patent No.: US 8,701,493 B2
(45) Date of Patent: Apr. 22, 2014

(54) VIBRATION MONITORING APPARATUS AND VIBRATION MONITORING METHOD

(75) Inventors: Masanobu Watanabe, Kanagawa-Ken (JP); Yasumi Kitajima, Tokyo (JP); Michio Sato, Kanagawa-Ken (JP); Mieko Sato, legal representative, Kanagawa-Ken (JP); Tsuyoshi Hagiwara, Kanagawa-Ken (JP); Masahiko Warashina, Kanagawa-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 950 days.

(21) Appl. No.: 12/677,999

(22) PCT Filed: Sep. 12, 2008

(86) PCT No.: PCT/JP2008/066578
§ 371 (c)(1),
(2), (4) Date: Apr. 21, 2010

(87) PCT Pub. No.: WO2009/035098
PCT Pub. Date: Mar. 19, 2009

(65) Prior Publication Data
US 2011/0154900 A1 Jun. 30, 2011

(30) Foreign Application Priority Data
Sep. 13, 2007 (JP) ................................. 2007-237591

(51) Int. Cl.
*G01N 29/00* (2006.01)
(52) U.S. Cl.
USPC ................................. 73/627; 376/249; 73/579

(58) Field of Classification Search
USPC ............. 73/597, 627, 628, 579; 376/249, 252
See application file for complete search history.

(56) References Cited

U.S. PATENT DOCUMENTS

| 3,753,852 | A | * | 8/1973 | Scott et al. ..................... 376/249 |
| 4,290,849 | A | * | 9/1981 | Uesugi et al. ................. 376/258 |
| 4,622,202 | A | * | 11/1986 | Yamada et al. ............... 376/246 |
| 4,655,992 | A | * | 4/1987 | McKnight et al. ............ 376/247 |
| 4,689,621 | A | * | 8/1987 | Kleinberg ................ 340/870.17 |
| 4,876,059 | A | * | 10/1989 | Conroy .......................... 376/247 |
| 4,943,683 | A | | 7/1990 | Utsunomiya et al. |
| 5,257,545 | A | * | 11/1993 | Au-Yang ......................... 73/597 |
| 5,327,783 | A | * | 7/1994 | Au-Yang ......................... 73/597 |
| 6,898,551 | B2 | * | 5/2005 | Samata et al. ................ 702/182 |

(Continued)

FOREIGN PATENT DOCUMENTS

| JP | 58-19300 U | 2/1983 |
| JP | 64-46694 A | 2/1989 |

(Continued)

*Primary Examiner* — Peter MacChiarolo
*Assistant Examiner* — Samir M Shah
(74) *Attorney, Agent, or Firm* — Foley & Lardner LLP

(57) ABSTRACT

The present invention provides a vibration monitoring apparatus that monitors vibration of a jet pump disposed in a reactor pressure vessel using ultrasonic wave, including: an ultrasonic sensor that is attached to an outside the reactor pressure vessel, and transmits and receives ultrasonic wave; a reflector that is mounted on a surface of a riser pipe of the jet pump, and includes a planar reflecting surface that can reflect ultrasonic wave; and a signal processing unit that performs signal processing of the ultrasonic wave transmitted by the ultrasonic sensor, reflected by the reflecting surface of the reflector, and received by the ultrasonic sensor, and measures a vibration amplitude of the riser pipe and calculates a vibration waveform.

20 Claims, 13 Drawing Sheets

(56) References Cited

U.S. PATENT DOCUMENTS

| | | | |
|---|---|---|---|
| 6,919,803 B2 * | 7/2005 | Breed | 340/539.14 |
| 7,627,441 B2 * | 12/2009 | Longsdorf et al. | 702/56 |
| 7,819,003 B2 * | 10/2010 | Breed et al. | 73/290 V |
| 8,054,203 B2 * | 11/2011 | Breed et al. | 340/931 |
| 2008/0236275 A1 * | 10/2008 | Breed et al. | 73/290 V |
| 2009/0282920 A1 * | 11/2009 | Sato et al. | 73/597 |
| 2012/0285246 A1 * | 11/2012 | Kuroda et al. | 73/590 |

FOREIGN PATENT DOCUMENTS

| | | | | |
|---|---|---|---|---|
| JP | 11-125688 A | | 5/1999 | |
| JP | 11125688 A | * | 5/1999 | G21C 17/00 |
| JP | 2004-361131 A | | 12/2004 | |

* cited by examiner

VIBRATION MONITORING APPARATUS AND VIBRATION MONITORING METHOD

CROSS REFERENCE TO RELATED APPLICATIONS

This application is based upon and claims the benefit of priority from the prior Japanese Patent Application No. 2007-237591, filed on Sep. 13, 2007, the entire contents of which is incorporated herein by reference.

TECHNICAL FIELD

Embodiments of the present invention relates to a vibration monitoring apparatus and a vibration method, and more particularly to apparatus and method for monitoring vibration of an object to be monitored, particularly, a structure inside a nuclear reactor (which will be simply referred as "reactor" hereinafter) disposed in a reactor pressure vessel such as a jet pump, disposed in a vessel.

BACKGROUND ART

In a boiling water reactor, a wedge is used in a riser bracket to reduce fluid vibration of a jet pump that is one of recirculation devices used for adjusting a flow rate of reactor water. However, wear due to the fluid vibration may degrade the wedge. Particularly, increasing the flow rate of the reactor water is supposed in increasing an output of an existing nuclear power plant, and in this case, it is predicted that a flow rate of the jet pump is increased to increase vibration of the jet pump. Thus, in terms of ensuring safety of the reactor, a technique is required of monitoring vibration of the jet pump and degradation of the wedge from outside a reactor pressure vessel during operation of the reactor.

As such a vibration monitoring unit, as shown in Japanese Unexamined Patent Application Publication (Patent Laid-Open Publication) No. 11-125688 (JP-A-11-125688) (Patent Document 1), a vibration monitoring apparatus for a structure inside a reactor using ultrasonic wave (ultrasound) is known. Further, Japanese Unexamined Patent Application Publication (Patent Laid-Open Publication) No. 2004-361131 (JP-A-2004-361131) (Patent Document 2) discloses a technique of separating a plurality of reflected waves and measuring and monitoring vibration displacement with high accuracy when the plurality of reflected waves are measured in an overlapping manner depending on the shape of an object to be monitored in using the same technique.

A jet pump is a core internal structure (in-core structure) disposed in a reactor pressure vessel, and an optical measurement unit can not be used to evaluate vibration via reactor pressure vessel and reactor water. A mechanical measurement unit such as a strain gage can be used but is actually difficult to use due to its complexity because a measurement line needs to be routed inside and outside a pressure boundary. Thus, it may be suitable that the measuring and monitoring unit using ultrasonic wave disclosed in Patent Document 1 is used to measure and monitor vibration of the jet pump from outside the reactor pressure vessel.

Meanwhile, for vibration of a jet pump, the existence of vibration modes is confirmed other than a vibration mode with vibration in a radial direction of a reactor pressure vessel (direction perpendicular to a longitudinal direction of the jet pump) as a low-order eigenmode. However, in both of the Patent Documents, vibration only in the same direction as the radius direction of the reactor pressure vessel, which is an ultrasonic wave incident direction, can be measured (monitored). A component of the jet pump has a curved surface, and there is a possibility that ultrasonic wave reflected by the surface of the jet pump can not be suitably received.

Further, wear due to fluid vibration may degrade the wedge of the jet pump, and the wear state needs to be checked. Generally, the wear state can be checked only in a state where the reactor pressure vessel is opened in a routine inspection (examination) during operation stop of the reactor. Thus, when it is found that the wear of the wedge extremely develops and the wedge needs to be replaced, entire preparation period for wedge replacement correspond, as it is, an extension period of a routine inspection period.

DISCLOSURE OF THE INVENTION

The present invention has been made in consideration of the above described circumstances, and a first object of the invention is to provide a vibration monitoring apparatus and a vibration monitoring method, which are achieved in view of the above-described circumstances, and can properly monitor vibration of an object to be monitored using ultrasonic wave even if the object to be monitored has a curved surface.

It is a second object of the present invention to provide a vibration monitoring apparatus and a vibration monitoring method, which can recognize a time series position change based on wear and degradation due to vibration of the object to be monitored, and indicate time for replacement of the object to be monitored before a routine inspection.

It is a third object of the present invention to provide a vibration monitoring apparatus and a vibration monitoring method, which can recognize a time series change of a vibration frequency at which a vibration amplitude of the object to be monitored is maximum, and indicate time for replacement of the object to be monitored before a routine inspection.

It is a fourth object of the present invention to provide a vibration monitoring apparatus and a vibration monitoring method, which can recognize a time series change of a maximum value of the vibration amplitude of the object to be monitored, and indicate time for replacement of the object to be monitored before a routine inspection.

A vibration monitoring apparatus according to the present invention, that monitors vibration of an object to be monitored disposed in a vessel using ultrasonic wave, comprises:

an ultrasonic sensor that is attached to an outside the vessel, and transmits and receives the ultrasonic wave;

a reflector that is mounted on a surface of the object to be monitored, and includes a planar reflecting surface that reflects ultrasonic wave; and a signal processing unit that performs signal processing of the ultrasonic wave transmitted by the ultrasonic sensor, reflected by the reflecting surface of the reflector, and received by the ultrasonic sensor, and measures vibration displacement of the object to be monitored.

A vibration monitoring method according to the present invention, for monitoring vibration of an object to be monitored disposed in a vessel using ultrasonic wave, comprises the steps of:

reflecting ultrasonic wave from a ultrasonic sensor attached to an outside the vessel by a planar reflecting surface of a reflector mounted on a surface of the object to be monitored, and then receiving the ultrasonic wave by the ultrasonic sensor; and performing signal processing of the ultrasonic wave received by the ultrasonic sensor and measuring vibration displacement of the object to be monitored.

Further, a vibration monitoring apparatus according to the present invention, that monitors a position change based on wear and degradation due to vibration of an object to be monitored disposed in a vessel using ultrasonic wave, comprises:

a plurality of ultrasonic sensors that are attached to an outside the vessel along a longitudinal direction of the object to be monitored, and transmit and receive ultrasonic wave;

a signal processing unit that performs signal processing of the ultrasonic wave transmitted by the ultrasonic sensors, reflected by the object to be monitored, and received by the ultrasonic sensors, and measures a position of the object to be monitored; and a calculation unit that accumulates a time series change of the position of the object to be monitored, compares the accumulated time series change of the position and position change data with development of wear of the object to be monitored, and predicts timing when the object to be monitored reaches an acceptable limit value of wear amount.

Further, a vibration monitoring method according to the present invention, for monitoring a position change based on wear and degradation due to vibration of an object to be monitored disposed in a vessel using ultrasonic wave, comprises the steps of;

reflecting ultrasonic wave from a plurality of ultrasonic sensors attached to an outside the vessel along a longitudinal direction of the object to be monitored by the object to be monitored, and then receiving the ultrasonic wave by the ultrasonic sensors;

performing signal processing of the ultrasonic wave received by the ultrasonic sensors and measuring a position of the object to be monitored; and comparing a time series change of the position of the object to be monitored and position change data with development of wear of the object to be monitored, and predicting timing when the object to be monitored reaches an acceptable wear amount.

Furthermore, a vibration monitoring apparatus according to the present invention, that monitors vibration of an object to be monitored disposed in a vessel using ultrasonic wave, comprising:

a plurality of ultrasonic sensors that are attached to an outside the vessel along a longitudinal direction the object to be monitored, and transmit and receive ultrasonic wave;

a signal processing unit that performs signal processing of the ultrasonic wave transmitted by the ultrasonic sensors, reflected by the object to be monitored, and received by the ultrasonic sensor, and measures a vibration amplitude of the object to be monitored;

a calculation unit that accumulates a time series change of the vibration amplitude of the object to be monitored; and a frequency analyzer that calculates a vibration frequency at which the vibration amplitude of the object to be monitored is maximum and the maximum amplitude from the time series change of the vibration amplitude of the object to be monitored, wherein the calculation unit or the frequency analyzer accumulates the time series change of the vibration frequency at which the vibration amplitude of the object to be monitored is at the maximum, and the calculation unit outputs a warning signal to a warning unit when the accumulated time series change of the vibration frequency reaches an acceptable limit value of a preliminarily calculated frequency change.

Furthermore, a vibration monitoring method according to the present invention, for monitoring vibration of an object to be monitored disposed in a vessel using ultrasonic wave, comprises the steps of:

reflecting ultrasonic wave from a plurality of ultrasonic sensors attached to an outside the vessel along a longitudinal direction of the object to be monitored by the object to be monitored, and then receiving the ultrasonic wave by the a ultrasonic sensors;

performing signal processing of the ultrasonic wave received by the ultrasonic sensors and measuring a vibration amplitude of the object to be monitored;

calculating a vibration frequency at which the vibration amplitude of the object to be monitored is maximum and the maximum amplitude from the time series change of the vibration amplitude of the object to be monitored; and issuing a warning when the time series change of the vibration frequency at which the vibration amplitude of the object to be monitored is maximum reaches acceptable limit value of a preliminarily calculated frequency change.

Still further, a vibration monitoring apparatus according to the present invention, that monitors vibration of an object to be monitored disposed in a vessel using ultrasonic wave, comprises:

a plurality of ultrasonic sensors that are attached to an outside the vessel along a longitudinal direction the object to be monitored, and transmit and receive ultrasonic wave;

a signal processing unit that performs signal processing of the ultrasonic wave transmitted by the ultrasonic sensors, reflected by the object to be monitored, and received by the ultrasonic sensor, and measures a vibration amplitude of the object to be monitored;

a calculation unit that accumulates a time series change of the vibration amplitude of the object to be monitored; and a frequency analyzer that calculates a vibration frequency at which the vibration amplitude of the object to be monitored is maximum and the maximum amplitude from the time series change of the vibration amplitude of the object to be monitored, wherein the calculation unit or the frequency analyzer accumulates the time series change of the maximum value of the vibration amplitude of the object to be monitored, and the calculation unit outputs a warning signal to a warning unit when the accumulated time series change of the maximum value of the vibration amplitude reaches an upper limit value of an acceptable range of a preliminarily calculated maximum value of the vibration amplitude.

Still further, a vibration monitoring method for monitoring vibration of an object to be monitored disposed in a vessel using ultrasonic wave, comprises the steps of reflecting ultrasonic wave from a plurality of ultrasonic sensors attached to an outside the vessel along a longitudinal direction of the object to be monitored by the object to be monitored, and then receiving the ultrasonic wave by the a ultrasonic sensors;

performing signal processing of the ultrasonic wave received by the ultrasonic sensors and measuring a vibration amplitude of the object to be monitored;

calculating a vibration frequency at which the vibration amplitude of the object to be monitored is maximum and the maximum amplitude from the time series change of the vibration amplitude of the object to be monitored; and issuing a warning when the time series change of a maximum value of the vibration amplitude of the object to be monitored reaches an upper limit value of an acceptable range of a preliminarily calculated maximum value of the vibration amplitude.

With the vibration monitoring apparatus and vibration monitoring method according to the present invention, even if the object to be monitored has a curved surface, the ultrasonic sensor can reliably receive the ultrasonic wave reflected by the reflecting surface of the reflector, and thus the vibration of the object to be monitored can be properly monitored using the ultrasonic wave.

With the vibration monitoring apparatus and vibration monitoring method according to the present invention, the time series position change based on wear and degradation due to vibration of the object to be monitored can be recognized, and time for replacement of the object to be monitored can be indicated before a routine inspection.

With the vibration monitoring apparatus and vibration monitoring method according to the present invention, the time series change of the vibration frequency at which the vibration amplitude of the object to be monitored is at the maximum can be recognized, and time for replacement of the object to be monitored can be indicated before a routine inspection.

With the vibration monitoring apparatus and vibration monitoring method according to the present invention, the time series change of the maximum value of the vibration amplitude of the object to be monitored can be recognized, and time for replacement of the object to be monitored can be indicated before a routine inspection.

BRIEF DESCRIPTION OF THE DRAWINGS

FIG. 2 (which includes FIGS. 2A, 2B and 2C) is view illustrating a jet pump (of the BWR) illustrated in FIG. 1.

FIG. 6 (which includes FIGS. 6A and 6B) is an explanatory view schematically illustrating a vibration monitoring apparatus according to a third embodiment of the present invention, FIG. 6A is a front view illustrating a jet pump on which a reflector is mounted in a resting state and FIG. 6B is an explanatory view schematically illustrating an example of a vibration mode of the jet pump illustrated in FIG. 6A together with an ultrasonic sensor or the like;

FIG. 7 (which includes FIGS. 7A and 7B) is an explanatory view schematically illustrating a vibration monitoring apparatus according to a fourth embodiment of the present invention, FIG. 7A is a front view illustrating a jet pump on which reflectors are mounted in a resting state and FIG. 7B is an explanatory view schematically illustrating an example of a vibration mode of the jet pump illustrated in FIG. 7A together with an ultrasonic sensor or the like;

FIG. 8 (which includes FIGS. 8A and 8B) is an explanatory view schematically illustrating a vibration monitoring apparatus (fifth vibration monitoring apparatus) according to a fifth embodiment of the present invention together with a jet pump.

FIG. 9 (which includes FIGS. 9A, 9B and 9C) is an explanatory view schematically illustrating a vibration monitoring apparatus (sixth vibration monitoring apparatus) according to a sixth embodiment of the present invention.

FIG. 15 (which includes FIGS. 15A and 15B) is an explanatory view schematically illustrating a vibration monitoring apparatus (ninth vibration monitoring apparatus) according to a ninth embodiment of the present invention.

BEST MODE FOR CARRYING OUT THE INVENTION

Now the best mode for carrying out the present invention will be described with reference to the drawings.

First Embodiment

FIGS. 1-3

Figure 1:
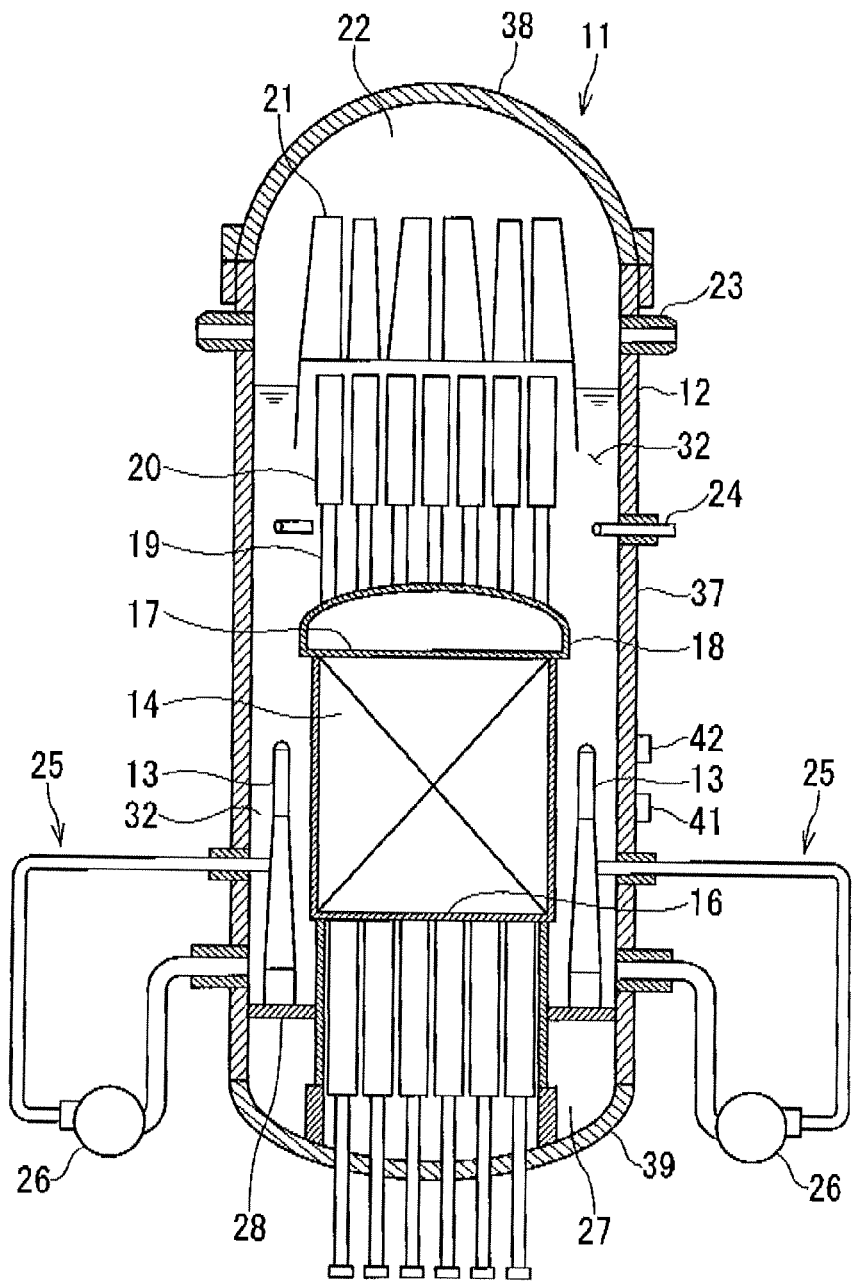
FIG. 1 is a vertical sectional view illustrating a boiling water reactor (BWR) to which a vibration monitoring apparatus according to a first embodiment of the present invention is applied.
Figure 2A:
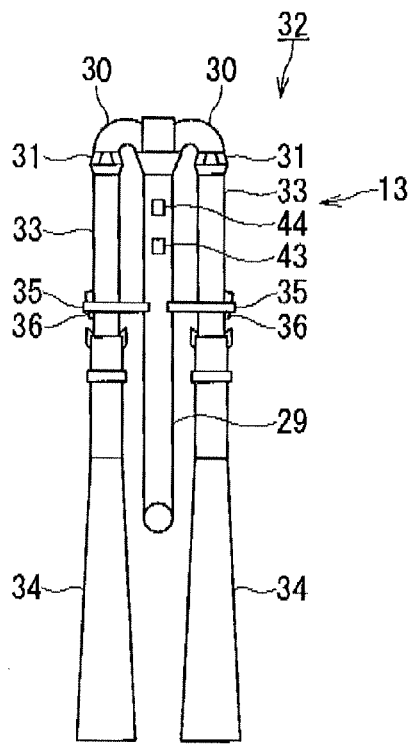
FIG. 2A is a front view illustrating the jet pump illustrated in FIG. 1.

FIG. 1 is a vertical sectional view illustrating a boiling water reactor to which a vibration monitoring apparatus according to a first embodiment of the present invention is applied. FIG. 2 is a front view illustrating a jet pump shown in FIG. 1, FIG. 3 is an enlarged configuration diagram of essential portions illustrating a configuration of the vibration monitoring apparatus together with a reactor pressure vessel and the jet pump shown in FIG. 1.

Figure 3:
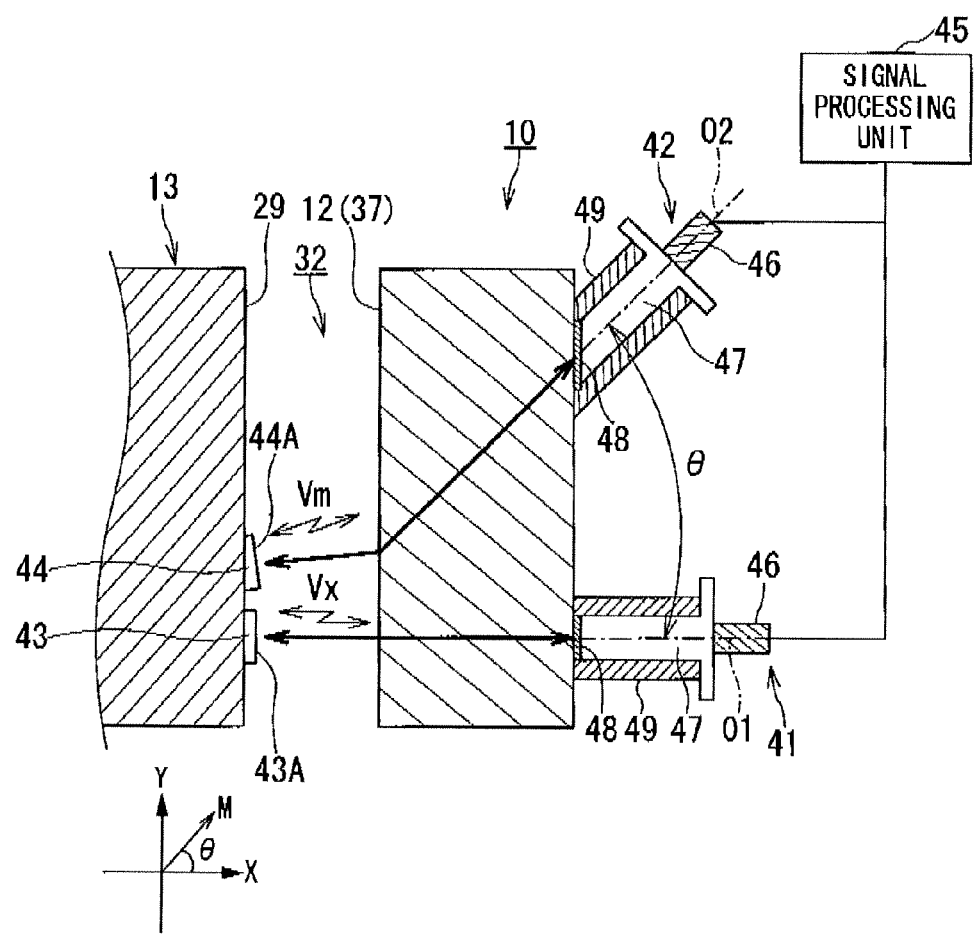
FIG. 3 is an enlarged configuration diagram of essential portions illustrating a configuration of the vibration monitoring apparatus together with a reactor pressure vessel and the jet pump.

The vibration monitoring apparatus 10 shown in FIG. 3 is applied to, for example, a boiling water reactor (hereinafter, referred to as "BWR") 11 shown in FIG. 1, and monitors vibration of a core internal structure, particularly, a jet pump 13, as an object to be monitored disposed in a reactor pressure vessel 12 as a vessel from outside the reactor pressure vessel 12 using ultrasonic wave (ultrasound).

As shown in FIG. 1, the BWR 11 houses a reactor core 14 in the reactor pressure vessel 12, and multiple fuel assemblies (not shown) that constitute the reactor core 14 are surrounded by a shroud 15, and supported by a reactor core support plate 16 and an upper grid plate 17. An upper portion of the shroud 15 is closed by a shroud head 18, and a steam-water separator 20 is mounted on the shroud head 18 via a stand pipe 19. In the reactor pressure vessel 12, a steam dryer 21 is provided above the steam-water separator 20.

From steam generated in the reactor core 14, water is separated by the steam-water separator 20, the steam is dried by the steam drier 21 and fed to an upper dome 22, and fed from a main steam nozzle 23 via a main steam system (not shown) to a turbine system (not shown). The steam having worked in the turbine system is condensed and supplied through a water supply pipe 24 into the reactor pressure vessel 12 as a coolant 32. The coolant (reactor water) 32 is increased in pressure by a recirculation pump 26 in a recirculation system 25, and guided to a lower plenum 27 below the reactor core 14 by a plurality of jet pumps 13 disposed in an annular portion between the reactor pressure vessel 12 and the shroud 15.

The plurality of jet pumps 13 are disposed on a pump deck 28 arranged in the annular portion between the reactor pressure vessel 12 and the shroud 15 at equally spaced intervals circumferentially of the reactor core 14. As shown FIG. 2A, each of the jet pumps 13 guides the coolant 32 increased in pressure by the recirculation pump 26 to a riser pipe 29, and further guides the coolant 32 via an elbow pipe 30 to a nozzle unit 31. The nozzle unit 31 takes in an ambient coolant 32, mixes the coolants 32 in an inlet mixer pipe 33, and discharges the coolants 32 from a jet pump diffuser 34 to below the reactor core 14.

Figure 2B:
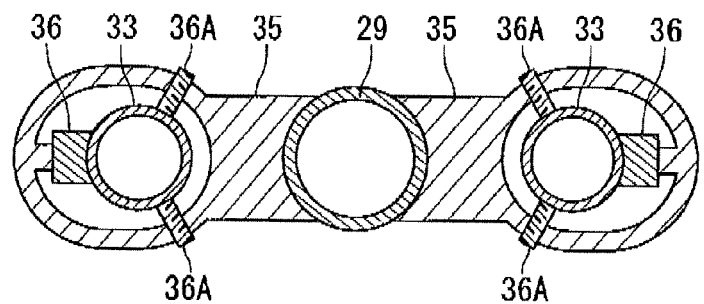
FIG. 2B is a horizontal sectional view illustrating the jet pump illustrated in FIG. 1.
Figure 2C:
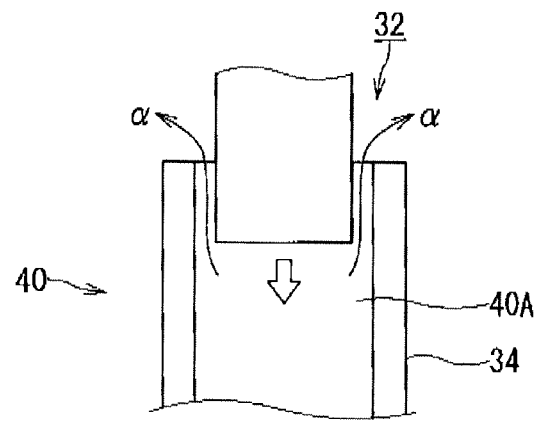
FIG. 2C is an enlarged vertical sectional view of essential portions illustrating the jet pump illustrated in FIG. 1.

As shown in FIG. 2C, a lowest end of the inlet mixer pipe 33 is fitted to the jet pump diffuser 34 with a gap 40A, and the fitting portion is referred to as a slip joint 40. As shown in FIG. 2B, the inlet mixer pipe 33 is supported using a riser bracket 35 mounted on the riser pipe 29 via a wedge 36 and a set screw 36A. Thus, central axes of the inlet mixer pipe 33 and the jet pump diffuser 34 are co-axially aligned. Thus, the inlet mixer pipe 33 is adjusted so as not to collide with the jet pump diffuser 34 by vibration due to a flow a of the coolant 32 flowing through the gap 40A of the slip joint 40.

However, vibration of the fluid flowing through the gap 40A of the slip joint 40 may cause sliding wear between the riser bracket 35 and the wedge 36 or between the riser bracket 35 and the set screw 36A, which may create a gap therebetween. If the gap is once created, variations in the flow of the fluid through the gap 40A of the slip joint 40 increase to further increase the sliding wear between the riser bracket 35 and the wedge 36 or between the riser bracket 35 and the set screw 36A, and finally, the inlet mixer pipe 33 may collide with the jet pump diffuser 34. The variations in the gap 40A of the slip joint 40 also affect performance of the jet pump 13. Thus, it is necessary to replace the wedge 36 or the set screw 36A, particularly the wedge 36, degraded with developed wear and always properly hold the gap 40A of the slip joint 40.

Incidentally, as shown in FIG. 1, the reactor pressure vessel 12 is configured so that an upper opening and a lower opening of a pressure vessel body 37 are closed by a vessel lid 38 and a lower mirror unit 39, respectively. The pressure vessel body 37 forms an annular portion in which the jet pump 13 is disposed, between the pressure vessel body 37 and the shroud 15.

In a nuclear power plant including the BWR 11 configured as described above, the action of the flow of the coolant 32 in the reactor pressure vessel 12 of the BWR 11 causes minute vibration of the jet pump 13 even in a normal operation state. The vibration monitoring apparatus 10 (FIG. 3) is provided to monitor such a vibration phenomenon from outside the reactor pressure vessel 12.

As shown in FIG. 3, the vibration monitoring apparatus 10 includes ultrasonic sensors 41 and 42 mounted on an outer surface of the reactor pressure vessel 12, reflectors 43 and 44 mounted on, for example, a surface of the riser pipe 29, which are portions to be monitored of the jet pump 13, and a signal processing unit 45 electrically connected to the ultrasonic sensors 41 and 42.

Each of the ultrasonic sensors 41 and 42 transmits and receives ultrasonic wave, and includes a vibrator 46, a focusing unit 47 and a couplant 48. Ultrasonic wave generated by the vibrator 46 is focused as a parallel wave by the focusing unit 47, and the parallel ultrasonic wave is transmitted via the couplant 48.

Each of the ultrasonic sensors 41 and 42 is secured to the outer surface of the reactor pressure vessel 12 by a securing jig 49. At this time, the ultrasonic sensor 41 is provided (attached) so that an axis O1 thereof is in a direction (X axis direction shown in FIG. 3) perpendicular to a longitudinal direction (Y axis direction shown in FIG. 3) of the riser pipe 29 of the jet pump 13. The ultrasonic sensor 42 is provided (attached) so that an axis O2 thereof is in a direction (M axis direction) at a predetermined angle $\theta$ from the X axis direction toward the Y axis direction.

The reflectors 43 and 44 are provided (mounted) in positions corresponding to the ultrasonic sensors 41 and 42, respectively, on the surface of the riser pipe 29 of the jet pump 13. Specifically, ultrasonic wave transmitted from each of the ultrasonic sensors 41 and 42 passes through the reactor pressure vessel 12 (pressure vessel body 37), propagates through the coolant (reactor water) 32, and is directed toward the riser pipe 29 of the jet pump 13. The reflectors 43 and 44 are provided in positions at which the ultrasonic waves from the ultrasonic sensors 41 and 42 reach the riser pipe 29. The reflectors 43 and 44 include planar reflecting surfaces 43A and 44A, respectively, capable of reflecting the ultrasonic wave. The reflectors 43 and 44 are provided, for example, adjacent to each other in close positions in the longitudinal direction (Y axis direction) of the riser pipe 29.

The ultrasonic waves reflected by the reflecting surface 43A of the reflector 43 and the reflecting surface 44A of the reflector 44 pass through paths in a direction opposite to the direction of the ultrasonic waves transmitted from the ultrasonic sensors 41 and 42 and propagated to the reflectors 43 and 44, reach the ultrasonic sensors 41 and 42, respectively, and are received by the ultrasonic sensors 41 and 42. The signal processing unit 45 performs signal processing of the ultrasonic waves received by the ultrasonic sensors 41 and 42, measures vibration amplitudes as vibration displacement in the X axis direction and the M axis direction of the riser pipe 29, and further calculates and measures a vibration amplitude in the Y axis direction.

That is, the signal processing unit 45 measures an amplitude Vx of vibration in the X axis direction of the riser pipe 29 using a propagation speed of the ultrasonic wave from a propagation time of the ultrasonic wave transmitted and received by the ultrasonic sensor 41, and calculates a vibration waveform in the X axis direction of the riser pipe 29 from the propagation time of the ultrasonic wave changing with time. Similarly, the signal processing unit 45 measures an amplitude Vm of vibration in the M axis direction of the riser pipe 29 from a propagation time of the ultrasonic wave transmitted and received by the ultrasonic sensor 42, and calculates a vibration waveform in the M axis direction. Then, the signal processing unit 45 calculates an amplitude Vy in the longitudinal direction (Y axis direction) of the riser pipe 29 perpendicular to the X axis direction from the amplitudes Vx and Vm in the X axis direction and the M axis direction by the expression below, and further calculates a vibration waveform in the Y axis direction.

$$Vy=(Vm^2-Vx^2)^{1/2}$$ [Expression 1]

As described above, the action of the flow of the coolant 32 causes minute vibration of the jet pump 13 even during normal operation of the nuclear power plant. Thus, the signal processing unit 45 predicts an amplitude level of minute vibration of the riser pipe 29 of the jet pump 13 during normal operation at least in one direction among the X axis direction, the M axis direction, and the Y axis direction. In case that an amplitude level actually measured and calculated exceeds the predicted amplitude level, the signal processing unit 45 determines (detects) abnormal vibration. Herein, prediction of the amplitude level during normal operation may be obtained by actually preliminarily measuring an amplitude or preliminarily calculating an amplitude by numerical analysis.

According to this (the first) embodiment, the apparatus and method according to this embodiment of the present invention provide following effects (advantages) (1) to (3) below.

(1) The ultrasonic waves transmitted from the ultrasonic sensors 41 and 42 are reflected by the reflectors 43 and 44 mounted on the surface of the riser pipe 29 of the jet pump 13 and including the planar reflecting surfaces 43A and 44A. Thus, even when the riser pipe 29 has a curved surface, the ultrasonic sensors 41 and 42 can reliably receive the ultrasonic waves reflected by the reflecting surface 43A of the reflector 43 and the reflecting surface 44A of the reflector 44. Thus, even vibration of the riser pipe 29 of the jet pump 13 having a curved surface can be properly monitored using ultrasonic wave.

(2) The ultrasonic sensor 41 is provided in the direction (X axis direction) perpendicular to the longitudinal direction (V axis direction) of the riser pipe 29 of the jet pump 13, the ultrasonic sensor 42 is provided in the M axis direction at the predetermined angle θ from the X axis direction, the amplitudes of vibration of the riser pipe 29 are measured in the X axis direction and the M axis direction, and from the amplitudes, the amplitude of vibration in the Y axis direction is also calculated. As such, the vibration of the riser pipe 29 can be captured in the two directions (X axis direction and Y axis direction) perpendicular to each other, and thus more satisfactory vibration monitoring can be achieved than vibration monitoring only in one direction (for example, X axis direction).

(3) In vibration monitoring of the riser pipe 29 of the jet pump 13, the amplitude level of the vibration of the riser pipe 29 during normal operation of the nuclear power plant is predicted, and abnormal vibration is detected when the amplitude of the vibration of the riser pipe 29 exceeds the amplitude level. Thus, the abnormal vibration of the riser pipe 29 can be quickly accommodated (suppressed).

Second Embodiment

FIGS. 4-5

Figure 4:
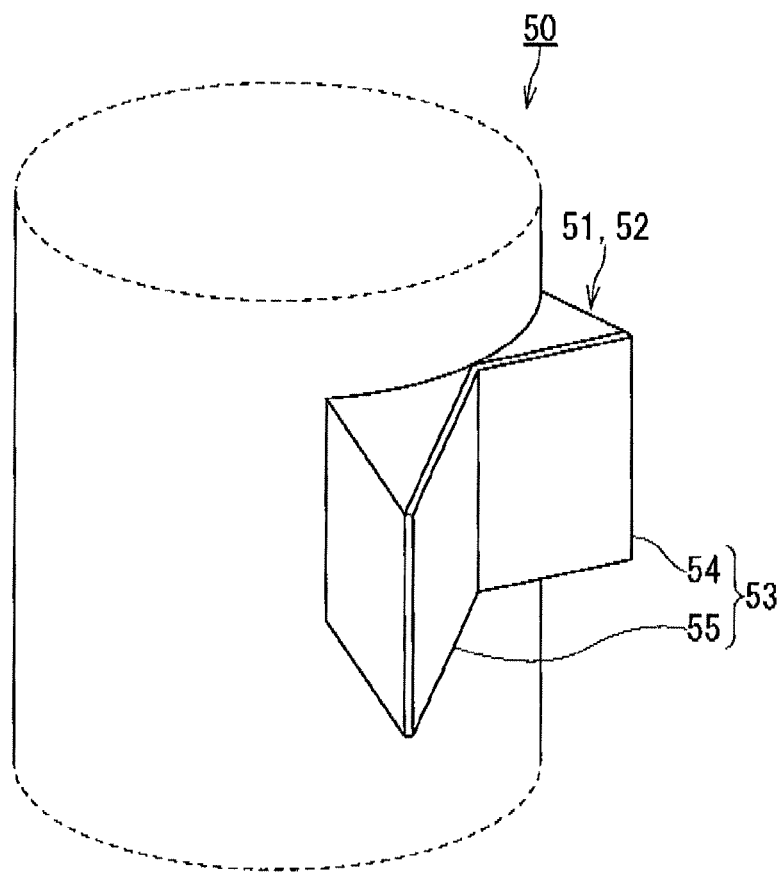
FIG. 4 is a perspective view illustrating a corner reflector as a reflector in a vibration monitoring apparatus according to a second embodiment of the present invention.

FIG. 4 is a perspective view illustrating a corner reflector as a reflector in a vibration monitoring apparatus according to a second embodiment of the present invention. In the second embodiment, the same components as in the first embodiment are denoted by the same reference numerals, and descriptions thereof will be simplified or omitted.

The vibration monitoring apparatus 50 according to this (the second) embodiment of the present invention is different from the vibration monitoring apparatus 10 according to the first embodiment of the present invention in that reflectors 51 and 52 using a corner reflector 53 are used as reflectors. The reflector 51 is mounted on a surface of a riser pipe 29 of a jet pump 13 so as to reflect ultrasonic wave from an ultrasonic sensor 41, like the reflector 43. The reflector 52 is mounted on the surface of the riser pipe 29 so as to reflect ultrasonic wave from an ultrasonic sensor 42, like the reflector 44.

Figure 5:
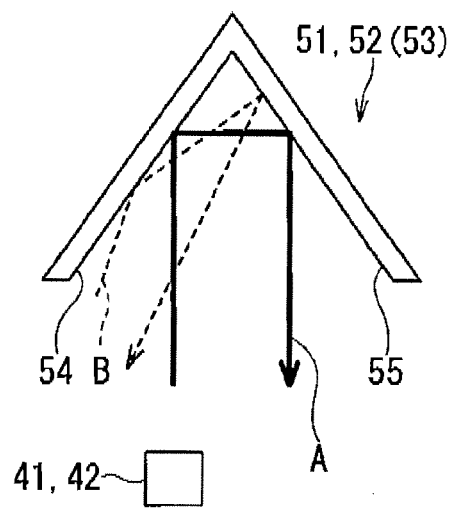
FIG. 5 is an explanatory view illustrating propagation paths of the ultrasonic wave reflected by the corner reflector illustrated in FIG. 4.

Each of the reflectors 43 and 44, described in first embodiment, has one plane as the reflecting surfaces 43A and 44A, while the corner reflector 53, described in this embodiment, has reflecting surfaces 54 and 55 that are two planes perpendicular to each other. Thus, the ultrasonic waves transmitted from the ultrasonic sensors 41 and 42 and having passed through a reactor pressure vessel 12 or the like are reflected by, for example, the reflecting surface 54 of the corner reflector 53 of the reflectors 51 and 52, and further reflected by the reflecting surface 55 in the same direction as the incident ultrasonic wave in a path parallel to the incident ultrasonic wave. Different propagation paths of the ultrasonic wave are shown by the solid line A and the broken line B in FIG. 5.

According to this (the second) embodiment, the apparatus and method according to this embodiment of the present invention provide the same advantages as the advantages (1) to (3), and additionally provide following advantages (4) and (5).

(4) As the reflectors 51 and 52 using the corner reflector 53 are mounted on the riser pipe 29 of the jet pump 13, the ultrasonic waves transmitted from the ultrasonic sensors 41 and 42 can be reflected by the reflecting surfaces 54 and 55 of the corner reflector 53 in the same direction as the incident direction. Thus, the ultrasonic sensors 41 and 42 can reliably receive the reflected ultrasonic waves to increase a signal-to-noise ratio, and vibration monitoring of the riser pipe 29 of the jet pump 13 can be achieved with high accuracy.

(5) The reflectors 51 and 52 reflect the ultrasonic waves transmitted from the ultrasonic sensor 41 or 42 in the parallel path. Thus, even when the ultrasonic sensors 41 and 42 can not be attached to supposed positions, the ultrasonic sensors 41 and 42 can be shifted to positions where the ultrasonic sensors can be attached to monitor the vibration of the riser pipe 29 of the jet pump 13.

Third Embodiment

FIG. 6

Figure 6A:
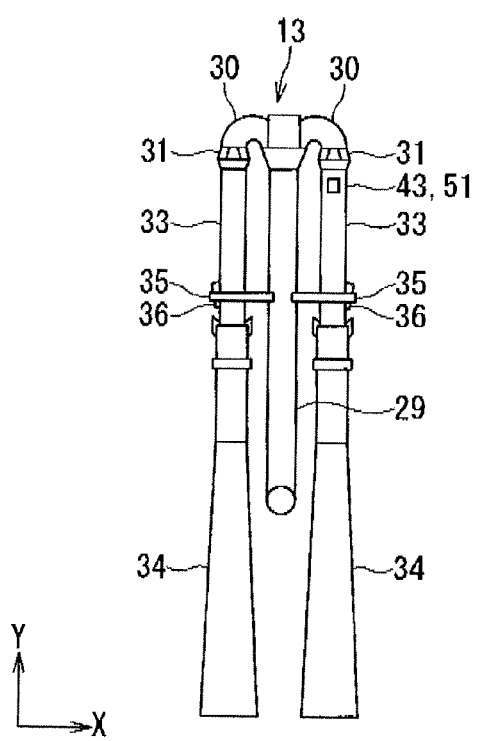
Figure 6B:
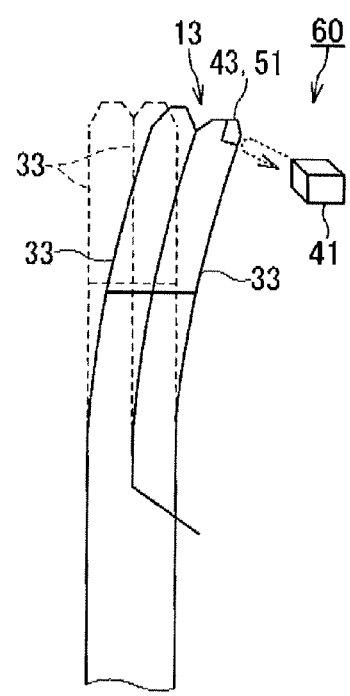

FIG. 6A is a front view illustrating a jet pump in a resting state on which a reflector is provided, and FIG. 6B schematically illustrates an example of a vibration mode of the jet pump together with an ultrasonic sensor or the like. For a vibration monitoring apparatus 60 according to a third embodiment of the present invention, the same components as in the vibration monitoring apparatus 10 according to a first embodiment of the present invention are denoted by the same reference numerals and descriptions thereof will be simplified or omitted.

Incidentally, in FIG. 6B, a resting state of the inlet mixer pipe 33 is shown by the broken line, and a vibration state thereof is shown by the solid line.

This (the third) embodiment is different from the first embodiment in that an object to be monitored is an inlet mixer pipe 33 having a curved surface of a jet pump 13, an ultrasonic sensor 42 is not provided, only an ultrasonic sensor 41 is provided in a direction (X axis direction) perpendicular to a longitudinal direction (Y axis direction) of the inlet mixer pipe 33, a reflector 44 is not provided, and a reflector 43 that reflects ultrasonic wave from the ultrasonic sensor 41 is mounted on a surface region of the inlet mixer pipe 33 with a relatively large amplitude in a normal vibration mode of the inlet mixer pipe 33.

The normal vibration mode of the inlet mixer pipe 33 is a vibration mode when the action of a flow of a coolant 32 causes minute vibration of the inlet mixer pipe 33 of the jet pump 13 in a reactor pressure vessel 12 during normal operation of a plant. The vibration mode may be preliminarily actually measured or preliminarily calculated by numerical analysis. The signal processing unit 45 detects abnormality when a measured amplitude of the inlet mixer pipe 33 exceeds an amplitude level in the normal vibration mode as in the first embodiment.

In FIG. 6 (FIGS. 6A and 6B), the reflector 43 is shown mounted on only one of the two pipes 33 of the jet pump 13, but the reflector 43 may be mounted on each of the two pipes 33, and the ultrasonic sensor 41 may be mounted on an outer surface of the reactor pressure vessel 12 correspondingly to each of the reflectors 43. Instead of the reflector 43, a reflector 51 using a corner reflector 53 may be mounted.

According to this (the third) embodiment, the apparatus and method according to this embodiment of the present invention provide the same advantages as the advantages (1), (3), (4) and (5) and additionally provide advantages a following advantage (6).

(6) The reflector 43 or 51 is provided in the region with a relatively large amplitude in the normal vibration mode of the inlet mixer pipe 33. The apparatus and method according to this embodiment of the present invention can increase vibration detection sensitivity of the inlet mixer pipe 33, and allows proper vibration monitoring of the inlet mixer pipe 33 to be performed.

Fourth Embodiment

FIG. 7

Figure 7A:
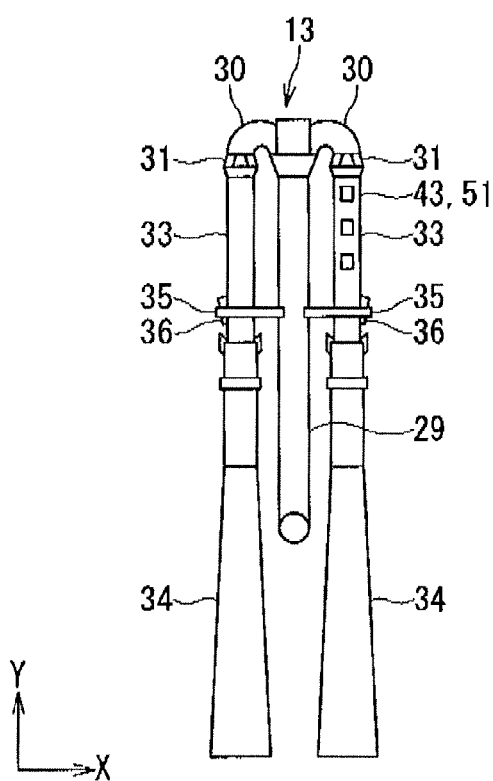
Figure 7B:
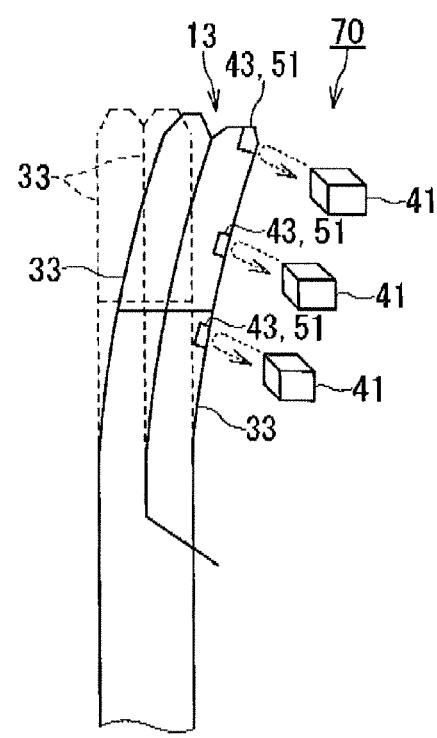

FIG. 7A is a front view illustrating a jet pump in a resting state on which reflectors are provided, and FIG. 7B schematically illustrates an example of a vibration mode of the jet pump together with an ultrasonic sensor or the like. For a vibration monitoring apparatus 70 according to a fourth embodiment of the present invention, the same components as in the vibration monitoring apparatus 10 according to a first embodiment of the present invention are denoted by the same reference numerals and descriptions thereof will be simplified or omitted. Incidentally, in FIG. 7B, a resting state of the inlet mixer pipe 33 is shown by the broken line, and a vibration state thereof is shown by the solid line.

A vibration monitoring apparatus 70 according to this (the fourth) embodiment of the present invention is different from the vibration monitoring apparatus 10 according to a first embodiment of the present invention in that an object to be monitored is an inlet mixer pipe 33 of a jet pump 13 having a curved surface, an ultrasonic sensor 42 is not provided (attached), a plurality of ultrasonic sensors 41 are attached to an outer surface of a reactor pressure vessel 12 along a longitudinal direction (Y axis direction) of the inlet mixer pipe 33 in a direction (X axis direction) perpendicular to the longitudinal direction of the inlet mixer pipe 33, a reflecting plate 44 is not provided, a plurality of reflectors 43 that reflect ultrasonic waves from the ultrasonic sensors 41 are provided along the longitudinal direction of the inlet mixer pipe 33 correspondingly to the ultrasonic sensors 41.

At least one of the pluralities of reflectors 43 mounted on the inlet mixer pipe 33 is preferably provided in a position with a relatively large amplitude in a normal vibration mode of the inlet mixer pipe 33.

The plurality of reflectors 43 are provided in the longitudinal direction (Y axis direction) of the inlet mixer pipe 33, and the plurality of ultrasonic sensors 41 are provided correspondingly to the reflectors 43. Thus, a signal processing unit 45 can calculate vibration waveforms at a plurality of points in the longitudinal direction of the inlet mixer pipe 33, that is, a vibration mode of the entire inlet mixer pipe 33 rather than a vibration waveform at one point of the inlet mixer pipe 33. The signal processing unit 45 detects abnormal vibration when the measured and calculated vibration mode of the entire inlet mixer pipe 33 is different from the normal vibration mode of the inlet mixer pipe 33.

In FIG. 7 (FIGS. 7A and 7B), the reflectors 43 are shown mounted on only one of the two pipes 33 of the jet pump 13, but the reflectors 43 may be mounted on each of the two pipes 33, and the ultrasonic sensors 41 may be mounted on the outer surface of the reactor pressure vessel 12 correspondingly to the reflectors 43. Instead of the reflector 43, a reflector 51 using a corner reflector 53 may be mounted.

According to this (the fourth) embodiment, the apparatus and method according to this embodiment of the present invention provide the same advantages as the advantages (1), (4) and (5) and additionally provide following advantage (7).

(7) The plurality of ultrasonic sensors 41 and the reflectors 43 or 51 are mounted on the outer surface of the reactor pressure vessel 12 and the surface of the inlet mixer pipe 33 along the longitudinal direction of the inlet mixer pipe 33, and the signal processing unit 45 measures and calculates the vibration mode of the entire inlet mixer pipe 33 and detects abnormal vibration when the vibration mode is different from the normal vibration mode, thereby allowing the abnormal vibration to be quickly accommodated (suppressed).

Fifth Embodiment

FIG. 8

Figures 8A, 8B:
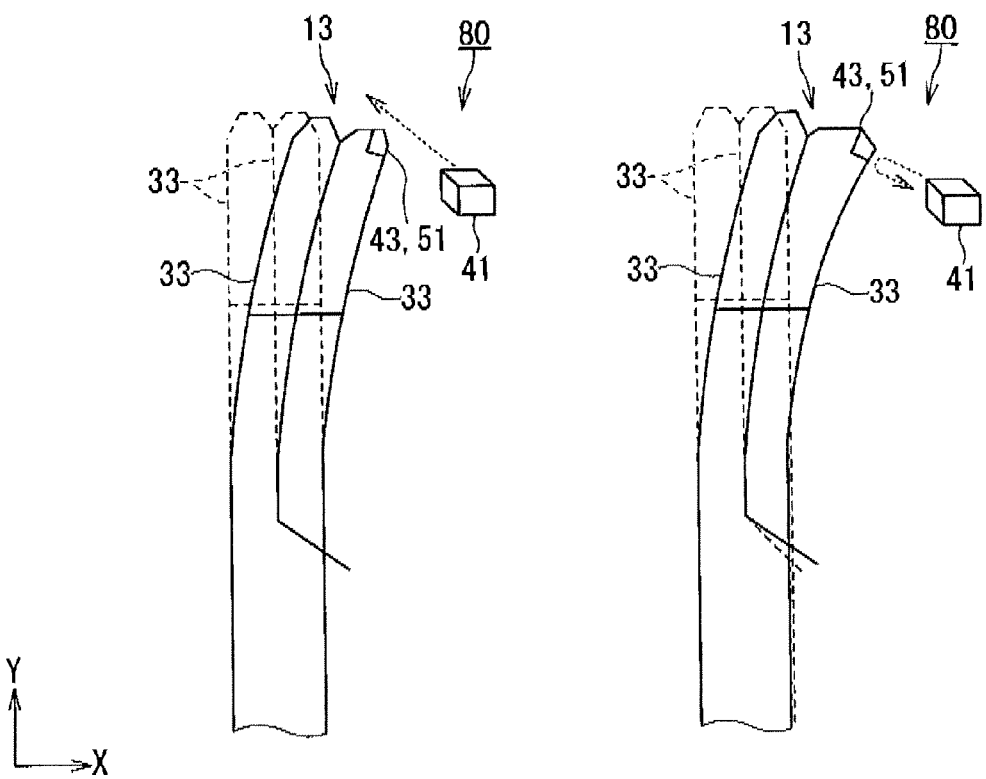
FIG. 8A is an explanatory view schematically illustrating the fifth vibration monitoring apparatus in a normal vibration mode of the jet pump and FIG. 8B is an explanatory view schematically illustrating the fifth vibration monitoring apparatus in a vibration mode of abnormal vibration of the jet pump.

FIG. 8 (FIG. 8A and FIG. 8B) show a vibration monitoring apparatus according to a fifth embodiment of the present invention together with a jet pump, FIG. 8A schematically illustrates a normal vibration mode of the jet pump, and FIG. 8B schematically illustrates a vibration mode of abnormal vibration of the jet pump. For a vibration monitoring apparatus 80 according to a fifth embodiment, the same components as in the vibration monitoring apparatus 10 according to a first embodiment of the present invention are denoted by the same reference numerals and descriptions thereof will be simplified or omitted.

A vibration monitoring apparatus 80 according to this (the fifth) embodiment is different from the vibration monitoring apparatus 10 according to a first embodiment of the present invention in that an object to be monitored is an inlet mixer pipe 33 of a jet pump 13 having a curved surface, an ultrasonic sensor 42 is not provided, an ultrasonic sensor 41 is provided in a direction (X axis direction) perpendicular to a longitudinal direction (Y axis direction) of the inlet mixer pipe 33, a reflector 44 is not provided, and a reflector 43 that reflects ultrasonic wave from the ultrasonic sensor 41 is mounted on a surface of the inlet mixer pipe 33. A further difference from the vibration monitoring apparatus 10 is that the ultrasonic sensor 41 is provided in a position where the ultrasonic sensor 41 can receive ultrasonic wave reflected by the reflector 43 in a vibration mode of abnormal vibration of the inlet mixer pipe 33 other than normal vibration.

Specifically, the ultrasonic sensor 41 is attached to an outer surface of a reactor pressure vessel 12 in a position where the ultrasonic sensor 41 can not receive ultrasonic wave reflected by the reflector 43 in normal vibration of the inlet mixer pipe 33 as shown in FIG. 8A, but can receive ultrasonic wave reflected by the reflector 43 when an amplitude becomes larger as in abnormal vibration of the inlet mixer pipe 33 as shown in FIG. 8B. Further, in this (the fifth) embodiment, instead of the reflector 43, a reflector 51 using a corner reflector 53 may be mounted.

According to this (the fifth) embodiment, the apparatus and method according to this embodiment of the present invention provide the same advantages as the advantages (1), (4) and (5) and additionally provide following advantage (8).

(8) The ultrasonic sensor 41 is attached to an outside of a region where the ultrasonic sensor 41 can not receive the ultrasonic wave reflected by the reflector 43 or 51 in the normal vibration mode of the inlet mixer pipe 33, but can receive the ultrasonic wave reflected by the reflector 43 or 51 in the vibration mode of the abnormal vibration of the inlet mixer pipe 33. Thus, the abnormal vibration of the inlet mixer pipe 33 can be satisfactorily detected and can be quickly accommodated.

Sixth Embodiment

FIG. 9

Figure 9A:
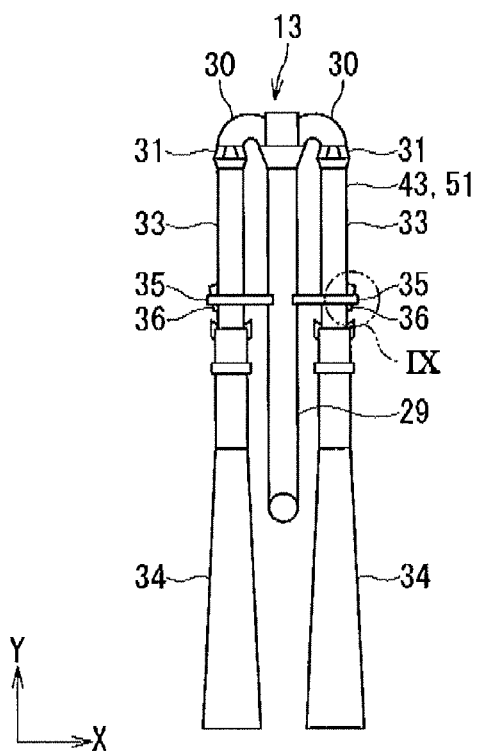
FIG. 9A is a front view illustrating a jet pump on which reflectors are mounted.
Figure 9B:
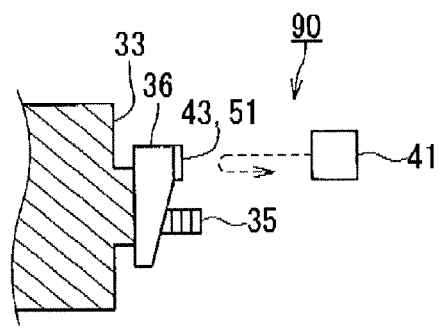
FIG. 9B is an enlarged view illustrating a portion IX in FIG. 9A, the view which is a sectional view illustrating a wedge in a normal position.
Figure 9C:
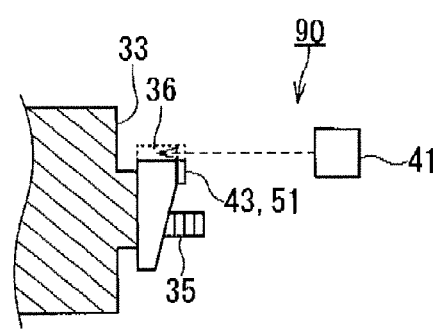
FIG. 9C is an enlarged view illustrating a portion IX in FIG. 9A, the view which is a sectional view illustrating a wedge in a moved position due to occurrence of wear.

FIG. 9 (FIGS. 9A, 9B and 9C) shows a vibration monitoring apparatus according to a sixth embodiment of the present invention, FIG. 9A is a front view illustrating a jet pump on which a reflector is provided, FIG. 9B is an enlarged view illustrating a portion IX in FIG. 9A, the view which is a sectional view illustrating a wedge in a normal position, and FIG. 9C is an enlarged view illustrating a portion IX in FIG. 9A, the view which is a sectional view illustrating a wedge in a moved position due to occurrence of wear. For a vibration monitoring apparatus 90 according to a sixth embodiment, the same components as in the vibration monitoring apparatus 10 are denoted by the same reference numerals and descriptions thereof will be simplified or omitted.

A vibration monitoring apparatus 90 according to this (the sixth) embodiment is different from the vibration monitoring apparatus 10 in that an object to be monitored is a wedge 36 of a jet pump 13 having a curved surface, an ultrasonic sensor 42 is not provided, an ultrasonic sensor 41 is provided in a direction (X axis direction) perpendicular to a longitudinal direction (Y axis direction) of the wedge 36, and a reflector 43 that reflects ultrasonic wave from the ultrasonic sensor 41 is mounted on the wedge 36. In this embodiment, the ultrasonic sensor 41 is provided in a position where the ultrasonic sensor 41 can not receive the ultrasonic wave reflected by the reflector 43 mounted on the wedge 36 when the wedge 36 is moved downward by wear due to vibration.

As described above, the wedge 36 is inserted between a riser bracket 35 and the inlet mixer pipe 33 to support the inlet mixer pipe 33 together with the riser bracket 35 mounted on a riser pipe 29. The wedge 36 is vibrated by the action of a flow of a coolant 32, and degraded by wear due to the vibration and moved downward, and thus may insufficiently support the inlet mixer pipe 33.

The ultrasonic sensor 41 receives ultrasonic wave transmitted from the ultrasonic sensor 41 and reflected by the reflector 43 mounted on the surface of the wedge 36, a signal processing unit 45 performs signal processing of the ultrasonic wave received by the ultrasonic sensor 41 and measures an amplitude of the vibration of the wedge 36 and calculates a vibration waveform, and thus the vibration of the wedge 36 is monitored. At this time, the signal processing unit 45 can detect abnormal vibration of the wedge 36 when the measured amplitude of the wedge 36 exceeds an amplitude level in normal vibration of the wedge 36.

When the wedge 36 wears due to the vibration and is moved downward, the ultrasonic wave from the ultrasonic sensor 41 is not reflected by the reflector 43, and the ultrasonic sensor 41 can not receive the ultrasonic wave reflected by the reflector 43, and then the signal processing unit 45 can detect the occurrence of wear and degradation of the wedge 36. Instead of the reflector 43, a reflector 51 using a corner reflector 53 may be provided.

According to this (the sixth) embodiment, the apparatus and method according to this embodiment of the present invention provide the same advantages as the advantages (1), (3), (4) and (5) and additionally provide following advantage (9).

(9) The reflector 43 or 51 is mounted on the wedge 36 of the jet pump 13, and the ultrasonic sensor 41 is provided in the position where the ultrasonic sensor 41 can not receive the ultrasonic wave reflected by the wedge 36 by the movement caused by the wear of the wedge 36 due to the vibration. Thus, monitoring the vibration allows the occurrence of the wear of the wedge 36 to be detected when the ultrasonic sensor 41 can not receive the ultrasonic wave, and allows the wear and degradation of the wedge 36 to be quickly accommodated.

Seventh Embodiment

FIGS. 10-12

Figure 10:
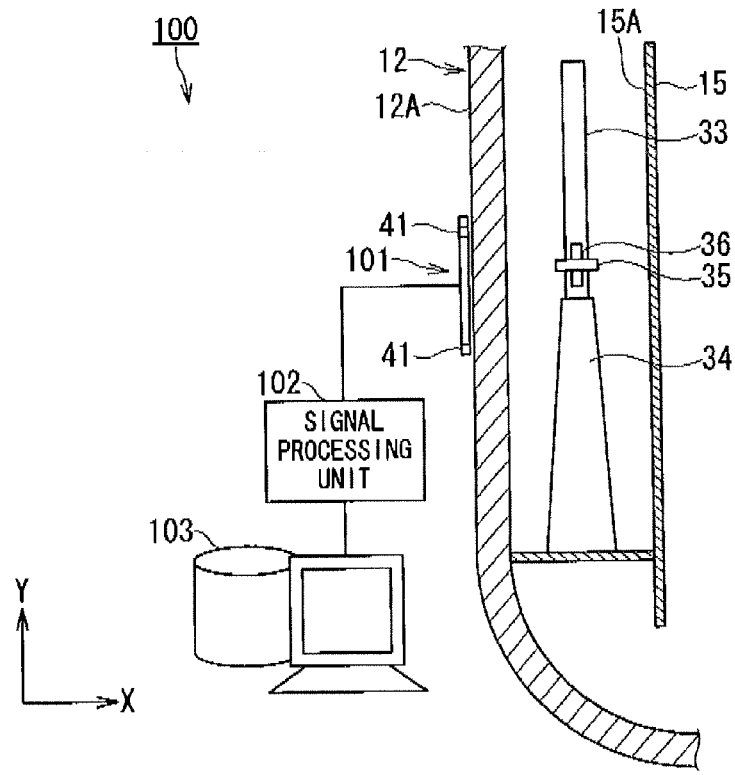
FIG. 10 is a configuration diagram of a vibration monitoring apparatus according to a seventh embodiment of the present invention.

FIG. 10 is a configuration diagram of a vibration monitoring apparatus according to a seventh embodiment of the present invention. For a vibration monitoring apparatus 100 according to a seventh embodiment, the same components as in the vibration monitoring apparatus 10 are denoted by the same reference numerals and descriptions thereof will be simplified or omitted.

A vibration monitoring apparatus 100 of this (the seventh) embodiment is different from the vibration monitoring apparatus 10 of the first embodiment in that an object to be monitored is a wedge 36 of a jet pump 13, an ultrasonic sensor 42 (FIG. 3) is not provided, a plurality of ultrasonic sensors 41 as an ultrasonic sensor group 101 are provided correspondingly to the wedge 36 on an outer surface 12A of a reactor pressure vessel 12 along a longitudinal direction (Y axis direction) of the wedge 36 in a direction (X axis direction) perpendicular to the longitudinal direction of the wedge 36, and monitor a time series height position change based on wear and degradation of the wedge 36 due to vibration using ultrasonic wave.

A reflector 44 (FIG. 3) is not provided. The reflector 43 (FIG. 3) may or may not be mounted on a side surface of the wedge 36 and an outer wall surface 15A of a shroud 15 correspondingly to the ultrasonic sensor 41. In this (the seventh) embodiment, an example without the reflector 43 is shown.

The vibration monitoring apparatus 100 according to this embodiment of the present invention includes the ultrasonic sensor group 101, and also a signal processing unit 102 and a processor 103. The signal processing unit 102 and the processor 103 may be integrally formed.

Figure 11:
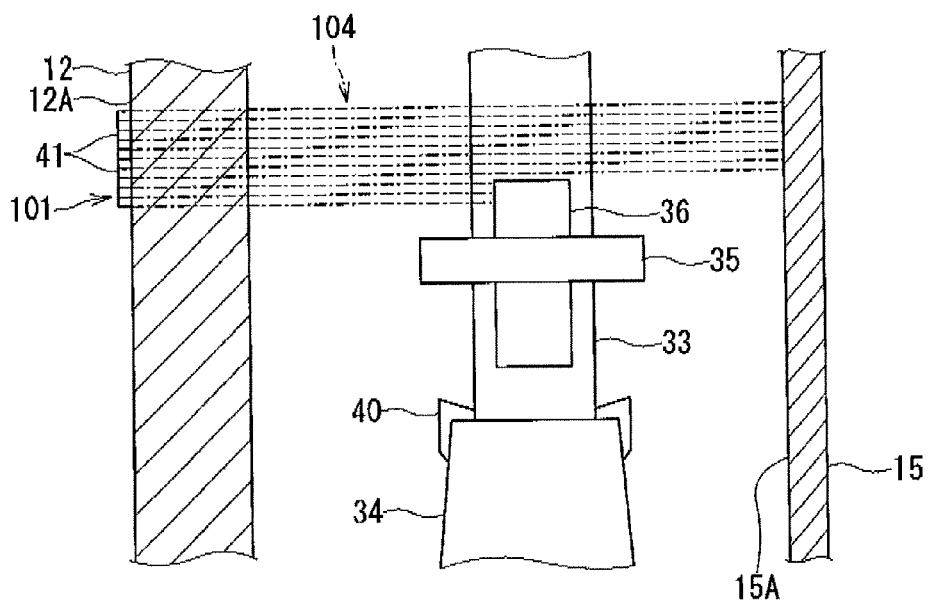
FIG. 11 is a sectional view, illustrating propagation paths of the ultrasonic wave, the sectional view which is enlarged at a portion of a part of the vibration monitoring apparatus illustrated in FIG. 10.

The signal processing unit 102 performs signal processing of ultrasonic wave transmitted by each sensor 41 of the ultrasonic sensor group 101, reflected by the wedge 36 or the shroud 15, and received by the ultrasonic sensor 41, that is, performs comparison processing of propagation time differences from transmission to receiving of the ultrasonic wave, and thus measures at which height position an upper end of the wedge 36 is located in the reactor pressure vessel 12. Reference numeral 104 shown in FIG. 11 denotes a propagation path of the ultrasonic wave.

Figure 12:
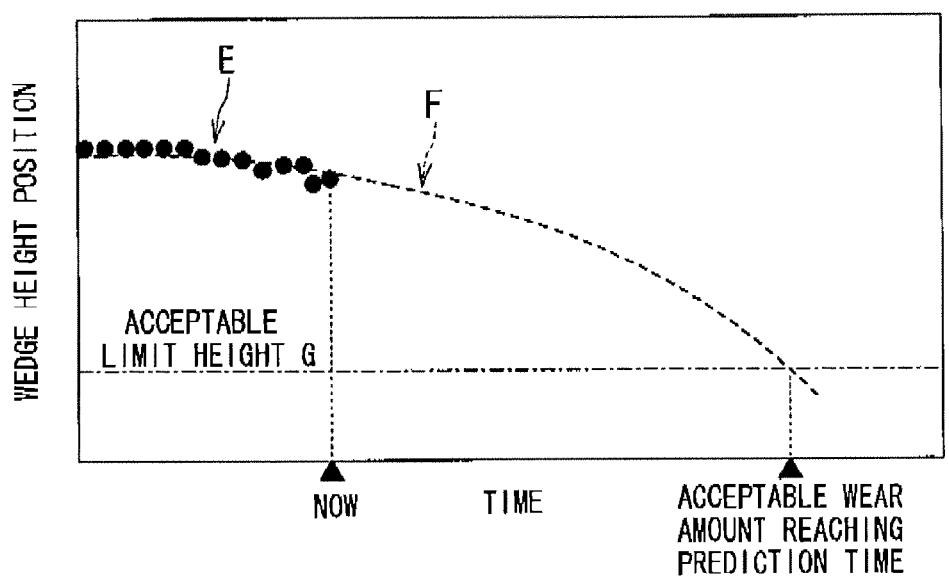
FIG. 12 is a graph showing a time series change of height position of a wedge.

When the wedge 36 wears due to vibration, the wedge 36 is gradually moved down by its own weight, and then the height position thereof changes. The processor 103 accumulates a time series change E (FIG. 12) of the height position of the wedge 36. The processor 103 stores position change data F (FIG. 12) that shows how the height position of the wedge 36 is changed with development of the wear and is separately calculated by vibration wear analysis or the like. The processor 103 compares the time series change E of the measured height position of the wedge 36 and the position change data F, and predicts timing when the wedge 36 reaches an acceptable limit height G corresponding to an acceptable wear amount.

According to this (the seventh) embodiment, the apparatus and method according to this embodiment of the present invention provide following advantage (10).

(10) The ultrasonic sensor group 101 and the signal processing unit 102 measure the height position of the wedge 36, the processor 103 accumulates the time series change of the height position of the wedge 36, and predicts the timing when the wedge 36 reaches the acceptable limit height G (acceptable wear amount). Thus, indicating the reaching timing allows the degree of degradation due to the wear of the wedge 36 or the life of the wedge 36 to be recognized during operation of the reactor. Thus, time for replacement of the wedge 36 can be recognized before a routine inspection of the reactor, thereby allowing preparation for replacement of the wedge 36 to be performed during operation of the reactor, and avoiding a situation where a preparation period for replacement of the wedge 36 extends a routine inspection period of the reactor.

Eighth Embodiment

Figure 13:
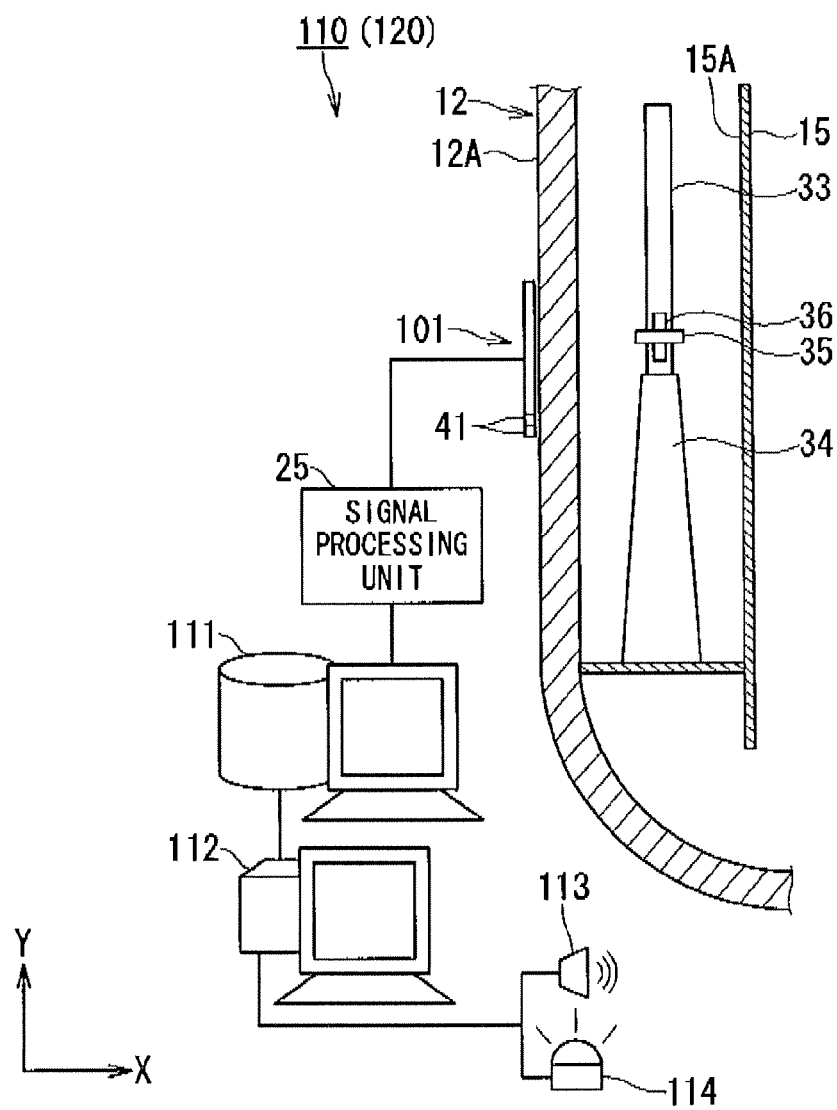
FIG. 13 is a configuration diagram of a vibration monitoring apparatus according to an eighth embodiment of the present invention.

FIGS. 13 and 14

FIG. 13 is a configuration diagram of a vibration monitoring apparatus according to an eighth embodiment of the present invention. For a vibration monitoring apparatus 110 according to an eighth embodiment, the same components as in the vibration monitoring apparatus 10 are denoted by the same reference numerals and descriptions thereof will be simplified or omitted.

A vibration monitoring apparatus 110 according to this (the eighth) embodiment is different from the vibration monitoring apparatus 10 in that an object to be monitored is a wedge 36 of a jet pump 13, an ultrasonic sensor 42 (FIG. 3) is not provided, a plurality of ultrasonic sensors 41 as an ultrasonic sensor group 101 are provided correspondingly to the wedge 36 on an outer surface 12A of a reactor pressure vessel 12 along a longitudinal direction (Y axis direction) of the wedge 36 in a direction (X axis direction) perpendicular to the longitudinal direction of the wedge 36, and monitor vibration of the wedge 36, a maximum value of a vibration amplitude of the wedge 36, a vibration frequency at which the vibration amplitude of the wedge 36 is maximum, or the like.

A reflector 44 (FIG. 3) is not provided. The reflector 43 (FIG. 3) may or may not be mounted on a side surface of the wedge 36 and an outer wall surface 15A of a shroud 15 correspondingly to the ultrasonic sensor 41. An example of the reflector 43 described in this (the eighth) embodiment is that the reflector 43 is not mounted on a side surface of the wedge 36 and an outer wall surface 15A of a shroud 15.

The vibration monitoring apparatus 110 of this embodiment includes the ultrasonic sensor group 101, and also a signal processing unit 25, a processor 111, a frequency analyzer 112, and an alarm unit 113 and a warning lamp 114 as a warning unit. The signal processing unit 25, the processor 111, and the frequency analyzer 112 may be integrally formed.

The signal processing unit 25 performs signal processing of ultrasonic wave transmitted by each ultrasonic sensor 41 of the ultrasonic sensor group 101, reflected by the wedge 36 and received by the ultrasonic sensor 41, measures an vibration amplitude of the wedge 36 in an X axis direction, and calculates a vibration waveform that is a time series change of the vibration amplitude.

Figure 14A:
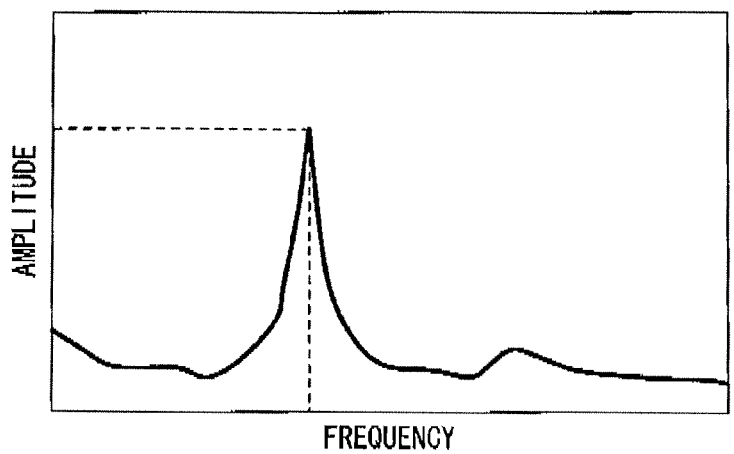
FIG. 14A is a graph showing a relation between the vibration amplitude of the wedge and the frequency.
Figure 14B:
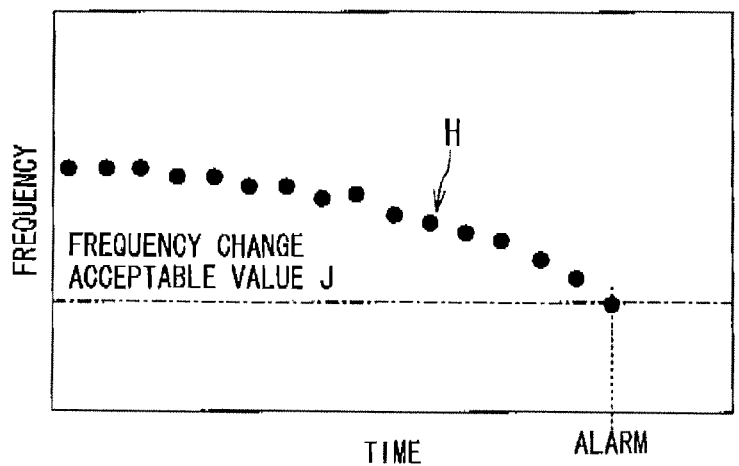
FIG. 14B is a graph showing a time series change of the frequency change at which the vibration amplitude of the wedge is maximum amplitude.
Figure 14C:
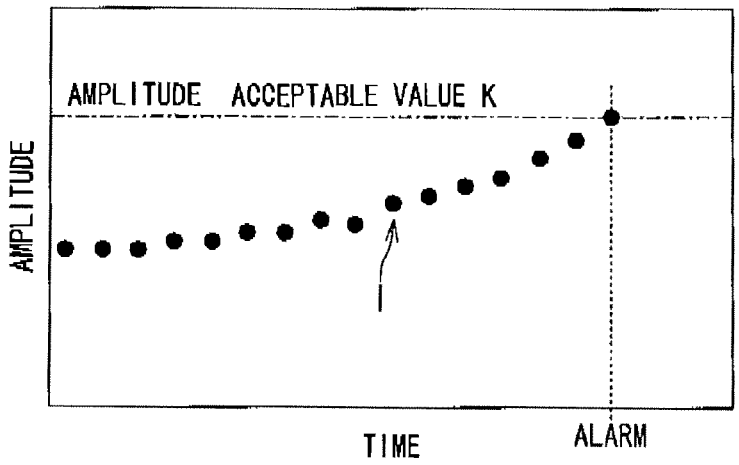
FIG. 14C is a graph showing a time series change of the maximum value of the vibration amplitude of the wedge.

While the processor 111 accumulates a time series change of the vibration amplitude of the wedge 36, the frequency analyzer 112 performs frequency analysis of the time series change accumulated by the processor 111, as shown in FIG. 14A. Thus, the frequency analyzer 112 calculates a vibration frequency at which the vibration amplitude of the wedge 36 is maximum amplitude and a maximum value of the vibration amplitude. A time series change H (FIG. 14B) of the vibration frequency at which the vibration amplitude of the wedge 36 is maximum amplitude and a time series change I (FIG. 14C) of the maximum value of the vibration amplitude of the wedge 36 are accumulated in the frequency analyzer 112 or the processor 111.

The processor 111 stores an acceptable value (limit value of an acceptable range) J of the frequency change at which the vibration amplitude of the wedge 36 is maximum amplitude and an acceptable value (limit value of an acceptable range) K of the maximum value of the vibration amplitude of the wedge 36, which are preliminarily calculated by vibration analysis. The processor 111 outputs a warning signal to the alarm unit 113 and the warning lamp 114 when the time series change H of the vibration frequency at which the vibration amplitude of the wedge 36 is maximum reaches the acceptable value J, or when the time series change I of the maximum value of the vibration amplitude of the wedge 36 reaches the acceptable value K. The alarm unit 113 and the warning lamp 114 receive the warning signal and issue (alarm) auditory and visual warnings, respectively.

According to this (the eighth) embodiment, the apparatus and method according to this embodiment of the present invention provide following advantage (11).

(11) The frequency analyzer 112 calculates the vibration frequency at which the vibration amplitude of the wedge 36 is maximum amplitude and the maximum value of the vibration amplitude from the time series change of the vibration amplitude of the wedge 36. In addition, the processor 111 operates the alarm unit 113 and the warning lamp 114 to indicate that effect when the time series change H of the vibration frequency at which the vibration amplitude of the wedge 36 is maximum reaches the acceptable value J or when the time series change I of the maximum value of the vibration amplitude of the wedge 36 reaches the acceptable value K. Thus, the degree of wear and degradation due to the vibration of the wedge 36 or the life of the wedge 36 can be recognized during operation of the reactor, and time for replacement of the wedge 36 can be recognized before a routine inspection of the reactor. As a result, as the user can start to prepare for replacement of the wedge 36 to be performed during operation of the reactor, a preparation period for replacement of the wedge 36 does not cause an extension of a routine inspection period of the reactor.

Ninth Embodiment

FIG. 15

Figure 15A:
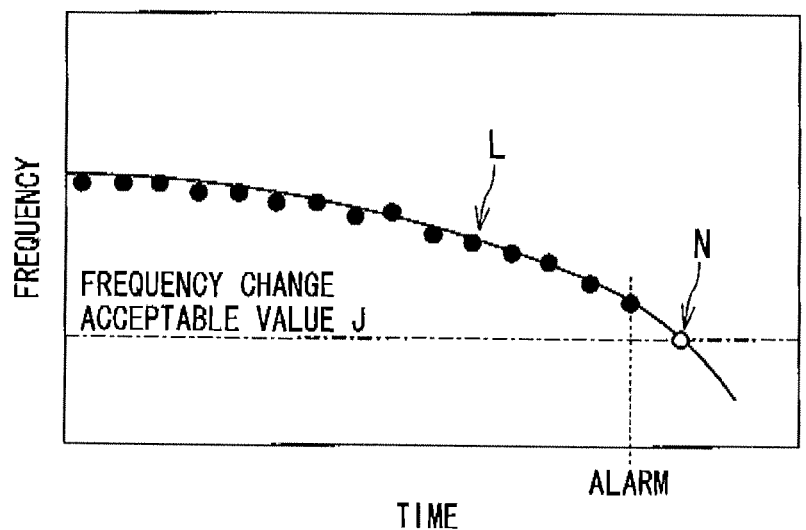
FIG. 15A is a graph for predicting a value of a vibration frequency at which a vibration amplitude of a wedge is maximum at the next future time interval.
Figure 15B:
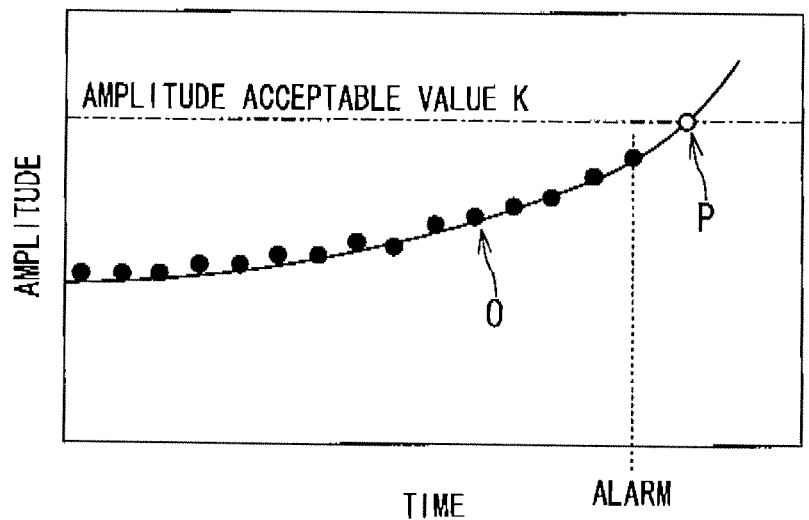
FIG. 15B is a graph for predicting a maximum value of the vibration amplitude of the wedge at the next future time interval.

FIG. 15 illustrates a vibration monitoring apparatus according to a ninth embodiment of the present invention, FIG. 15A is a graph for predicting a value of a vibration frequency at which a vibration amplitude of a wedge is maximum at the next future time interval, and FIG. 15B is a graph for predicting a maximum value of the vibration amplitude of the wedge at the next future time interval. For a vibration monitoring apparatus 120 according to a ninth embodiment, the same components as in the vibration monitoring apparatuses 10 and 110 are denoted by the same reference numerals and descriptions thereof will be simplified or omitted.

A vibration monitoring apparatus 120 (FIG. 13) of this (the ninth) embodiment is different from the vibration monitoring apparatus 110 of the eighth embodiment in that the value of the vibration frequency at which the vibration amplitude of the wedge 36 is maximum is predicted, or the maximum value of the vibration amplitude of the wedge 36 is predicted, and a warning is issued (alarmed) when the predicted value reaches an acceptable value (limit value of an acceptable range) J or K.

Specifically, the processor 111 of this embodiment samples a time series change of the vibration frequency at which the vibration amplitude of the wedge 36 is maximum accumulated in the processor 111 or the frequency analyzer 112 at regular time intervals, and plots as indicated by black circles in FIG. 15A. The processor 111 calculates an extrapolation function of an (N−1) algebraic expression from N time-series data of similar vibration frequencies of the wedge 36 sampled before, and uses the extrapolation function to calculate and store a predicted frequency curve L.

The processor 111 compares the time series change of the vibration frequency sampled at regular time intervals and the predicted frequency curve L, and predicts the value of the vibration frequency at which the vibration amplitude is maximum at the next future time interval as a predicted value N. Then, the processor 111 outputs a warning signal to the alarm unit 113 and the warning lamp 114 to cause the alarm unit 113 to output an auditory warning and cause the warning lamp 114 to output a visual warning when the predicted value N reaches the acceptable value J of the frequency change preliminarily calculated by numerical analysis.

The processor 111 of this embodiment samples the time series change of the maximum value of the vibration amplitude of the wedge 36 accumulated in the processor 111 or the frequency analyzer 112 at regular time intervals, and plots as indicated by black circles in FIG. 15B. The processor 111 calculates an extrapolation function of an (N−1) algebraic expression from N time-series data of similar maximum values of the vibration amplitude of the wedge 36 sampled before, and uses the extrapolation function to calculate and store a predicted amplitude curve O.

The processor 111 compares the time series change of the maximum value of the vibration amplitude sampled at regular time intervals and the predicted amplitude curve O, and predicts the maximum value of the vibration amplitude at the next future time interval as a predicted value P. Then, the processor 111 outputs a warning signal to the alarm unit 113 and the warning lamp 114 to cause the alarm unit 113 to output an auditory warning and cause the warning lamp 114 to output a visual warning when the predicted value P reaches the acceptable value K of the maximum value of the vibration amplitude preliminarily calculated by numerical analysis.

According to this (the ninth) embodiment, the apparatus and method according to this embodiment of the present invention provide following advantage (12).

(12) When the predicted value N at the next future time interval of the vibration frequency at which the vibration amplitude of the wedge 36 takes a maximum amplitude reaches the acceptable value J of the frequency change, or the predicted value P at the next future time interval of the maximum value of the vibration amplitude of the wedge 36 reaches the acceptable value K of the maximum value of the vibration amplitude, the alarm unit 113 is operated and the warning lamp 114 is lit. Thus, the apparatus and method according to this embodiment of the present invention can provide the same advantage as those of the eighth embodiment, and can ensure a sufficient preparation period for replacement of the wedge 36.

The present invention has been described above based on the embodiments, but are not limited thereto. For example, the same advantages can be obtained by forming the reflectors 43, 44, 51 and 52 integrally with the object to be monitored, or forming a reflecting surface on a part of the object to be monitored. In this (the ninth) embodiment, the object to be monitored is the jet pump 13, but may be a different reactor internal such as the shroud 15 that vibrates in the reactor pressure vessel 12 or the steam-water separator 20. Furthermore, the object to be monitored may be a device disposed in a vessel or a tank other than the reactor pressure vessel 12, an inner pipe of a double pipe, or a tube in a heat exchanger.

The invention claimed is:

1. A vibration monitoring apparatus that monitors vibration of a component of a jet pump to be monitored disposed in a reactor pressure vessel using an ultrasonic wave, comprising:
   at least one ultrasonic sensor that is attached to an outside of the reactor pressure vessel, and transmits and receives the ultrasonic wave;
   at least one reflector that is mounted on a curved surface of the component of the jet pump to be monitored, and includes a planar reflecting surface that reflects the ultrasonic wave; and
   a signal processing unit that performs signal processing of the ultrasonic wave transmitted by the ultrasonic sensor, reflected by the reflecting surface of the reflector, and received by the ultrasonic sensor, and measures a vibration displacement of the component of the jet pump to be monitored.

2. The vibration monitoring apparatus according to claim 1, wherein the signal processing unit detects abnormal vibration when an amplitude level as the measured vibration displacement of the component of the jet pump to be monitored exceeds a normal amplitude level of the component of the jet pump to be monitored.

3. The vibration monitoring apparatus according to claim 1, wherein the reflector is provided in a region with a relatively large amplitude in a normal vibration mode of the component of the jet pump to be monitored.

4. The vibration monitoring apparatus according to claim 1, wherein a plurality of reflectors are arranged along a vertical direction of the component of the jet pump to be monitored and a plurality of ultrasonic sensors are attached to the outside of the reactor pressure vessel correspondingly to the reflectors.

5. A vibration monitoring apparatus that monitors vibration of a component of a jet pump to be monitored disposed in a reactor pressure vessel using an ultrasonic wave, comprising:
- at least one ultrasonic sensor that is attached to an outside of the reactor pressure vessel, and transmits and receives the ultrasonic wave;
- at least one reflector that is mounted on a surface of the component of the jet pump to be monitored, and includes a planar reflecting surface that reflects the ultrasonic wave; and
- a signal processing unit that performs signal processing of the ultrasonic wave transmitted by the ultrasonic sensor, reflected by the planar reflecting surface of the reflector, and received by the ultrasonic sensor, and measures a vibration displacement of the component of the jet pump to be monitored, wherein
- a plurality of ultrasonic sensors, one ultrasonic sensor provided in each of a direction perpendicular to a vertical direction of the component of the jet pump to be monitored and a direction at a predetermined angle to the vertical direction,
- reflectors are mounted on the component of the jet pump to be monitored correspondingly to the ultrasonic sensors, and
- the signal processing unit calculates a vibration displacement, in the direction perpendicular to the vertical direction and in the vertical direction of the component of the jet pump to be monitored.

6. A vibration monitoring apparatus that monitors vibration of a component of a jet pump to be monitored disposed in a reactor pressure vessel using an ultrasonic wave, comprising:
- at least one ultrasonic sensor that is attached to an outside of the reactor pressure vessel, and transmits and receives the ultrasonic wave;
- at least one reflector that is mounted on a surface of the component of the jet pump to be monitored, and includes a planar reflecting surface that reflects the ultrasonic wave; and
- a signal processing unit that performs signal processing of the ultrasonic wave transmitted by the ultrasonic sensor, reflected by the planar reflecting surface of the reflector, and received by the ultrasonic sensor, and measures a vibration displacement of the component of the jet pump to be monitored,
- wherein the reflector is a corner reflector including a first planar reflecting surface and a second planar reflecting surface disposed perpendicular to the first planar reflecting surface, the first and second reflecting surfaces being configured to reflect the ultrasonic wave such that an incident ultrasonic wave is reflected from the first reflecting surface to the second reflecting surface, and then reflected from the second reflecting surface to the ultrasonic sensor.

7. A vibration monitoring apparatus that monitors vibration of a component of a jet pump to be monitored disposed in a reactor pressure vessel using an ultrasonic wave, comprising:
- at least one ultrasonic sensor that is attached to an outside of the reactor pressure vessel, and transmits and receives the ultrasonic wave;
- at least one reflector that is mounted on a surface of the component of the jet pump to be monitored, and includes a planar reflecting surface that reflects the ultrasonic wave; and
- a signal processing unit that performs signal processing of the ultrasonic wave transmitted by the ultrasonic sensor, reflected by the planar reflecting surface of the reflector, and received by the ultrasonic sensor, and measures a vibration displacement of the component of the jet pump to be monitored,
- wherein the ultrasonic sensor is attached to a region where the ultrasonic sensor is configured to receive the ultrasonic wave reflected by the reflector mounted on the component of the jet pump to be monitored in a vibration mode of an abnormal vibration other than normal vibration of the component of the jet pump to be monitored, and is configured to not receive the ultrasonic wave reflected by the reflector mounted on the component of the jet pump to be monitored in a vibration mode of the normal vibration.

8. A vibration monitoring apparatus that monitors vibration of a component of a jet pump to be monitored disposed in a reactor pressure vessel using an ultrasonic wave, comprising:
- at least one ultrasonic sensor that is attached to an outside of the reactor pressure vessel, and transmits and receives the ultrasonic wave;
- at least one reflector that is mounted on a surface of the component of the jet pump to be monitored, and includes a planar reflecting surface that reflects the ultrasonic wave; and
- a signal processing unit that performs signal processing of the ultrasonic wave transmitted by the ultrasonic sensor, reflected by the planar reflecting surface of the reflector, and received by the ultrasonic sensor, and measures a vibration displacement of the component of the jet pump to be monitored, wherein
- the component of the jet pump is a wedge of the jet pump, and
- when the wedge of the jet pump is displaced due to wear and degradation of the wedge, the ultrasonic wave is not reflected by the reflector, the ultrasonic sensor does not receive the ultrasonic wave, and the signal processing unit can detect an occurrence of wear and degradation of the wedge.

9. A vibration monitoring apparatus that monitors a position change based on wear and degradation due to vibration of a component of a jet pump to be monitored disposed in a reactor pressure vessel using an ultrasonic wave, comprising:
- a plurality of ultrasonic sensors that are attached to an outside of the reactor pressure vessel along a longitudinal direction of the component of the jet pump to be monitored, the plurality of ultrasonic sensors configured to transmit and receive the ultrasonic wave;
- a signal processing unit that performs signal processing of the ultrasonic wave transmitted by the ultrasonic sensors, reflected by the component of the jet pump to be monitored, and received by the ultrasonic sensors, and measures a position of the component of the jet pump to be monitored; and
- a calculation unit that accumulates a time series change of the position of the component of the jet pump to be monitored, compares the accumulated time series change of the position and position change data, and predicts a time when the component of the jet pump to be monitored will reach an acceptable limit value of wear amount,
- wherein the position of the component of the jet pump to be monitored changes based on wear and degradation due to the vibration of the component of the jet pump to be monitored.

10. The vibration monitoring apparatus according to claim 9, wherein the component of the jet pump is a wedge of the jet pump disposed in the reactor pressure vessel.

11. A vibration monitoring apparatus that monitors vibration of a component of a jet pump to be monitored disposed in a reactor pressure vessel using an ultrasonic wave, comprising:
   a plurality of ultrasonic sensors that are attached to an outside of the reactor pressure vessel along a longitudinal direction the component of the jet pump to be monitored, the plurality of ultrasonic sensors configured to transmit and receive the ultrasonic wave;
   at least one reflector that is mounted on a curved surface of the component of the jet pump to be monitored, and includes a planar reflecting surface that reflects the ultrasonic wave;
   a signal processing unit that performs signal processing of the ultrasonic wave transmitted by the ultrasonic sensors, reflected by the reflector mounted on the curved surface of the component of the jet pump to be monitored, and received by the ultrasonic sensor, and measures a vibration amplitude of the component of the jet pump to be monitored;
   a calculation unit that accumulates a time series change of the vibration amplitude of the component of the jet pump to be monitored; and
   a frequency analyzer that calculates a vibration frequency at which the vibration amplitude of the component of the jet pump to be monitored is a maximum and a maximum amplitude from the time series change of the vibration amplitude of the component of the jet pump to be monitored,
   wherein the calculation unit or the frequency analyzer accumulates the time series change of the vibration frequency at which the vibration amplitude of the component of the jet pump to be monitored is at the maximum, and
   the calculation unit outputs a warning signal to a warning unit when the accumulated time series change of the vibration frequency reaches an acceptable limit value of a preliminarily calculated frequency change.

12. The vibration monitoring apparatus according to claim 11, wherein the component of the jet pump to be monitored is a wedge of a jet pump disposed in the reactor pressure vessel.

13. The vibration monitoring apparatus according to claim 11, wherein the calculation unit samples the time series change of the vibration frequency at which the vibration amplitude is the maximum accumulated in the calculation unit or the frequency analyzer at regular time intervals, calculates a predicted frequency curve from time-series data of similar vibration frequencies sampled before, predicts a value of the vibration frequency at which the vibration amplitude is maximum at a next time interval from the sampled time series change of the vibration frequency and the predicted frequency curve, and outputs a warning signal to a warning unit when the predicted value reaches an acceptable value of a preliminarily calculated frequency change.

14. A vibration monitoring apparatus that monitors vibration of a component of a jet pump to be monitored disposed in a reactor pressure vessel using an ultrasonic wave, comprising:
   a plurality of ultrasonic sensors that are attached to an outside of the reactor pressure vessel along a longitudinal direction the component of the jet pump to be monitored, the plurality of ultrasonic sensors being configured to transmit and receive the ultrasonic wave;
   at least one reflector that is mounted on a curved surface of the component of the jet pump to be monitored, and includes a planar reflecting surface that reflects the ultrasonic wave;
   a signal processing unit that performs signal processing of the ultrasonic wave transmitted by the ultrasonic sensors, reflected by the reflector mounted on the curved surface of the component of the jet pump to be monitored, and received by the ultrasonic sensor, and measures a vibration amplitude of the component of the jet pump to be monitored;
   a calculation unit that accumulates a time series change of the vibration amplitude of the component of the jet pump to be monitored; and
   a frequency analyzer that calculates a vibration frequency at which the vibration amplitude of the component of the jet pump to be monitored is a maximum and a maximum amplitude from the time series change of the vibration amplitude of the component of the jet pump to be monitored,
   wherein the calculation unit or the frequency analyzer accumulates the time series change of the maximum value of the vibration amplitude of the component of the jet pump to be monitored, and
   the calculation unit outputs a warning signal to a warning unit when the accumulated time series change of the maximum value of the vibration amplitude reaches an upper limit value of an acceptable range of a preliminarily calculated maximum value of the vibration amplitude.

15. The vibration monitoring apparatus according to claim 14, wherein the component of the jet pump to be monitored is a wedge of the jet pump disposed in the reactor pressure vessel.

16. The vibration monitoring apparatus according to claim 14, wherein the calculation unit samples the time series change of the maximum value of the vibration amplitude accumulated in the calculation unit or the frequency analyzer at regular time intervals, calculates a predicted amplitude curve from time-series data of similar maximum values of the vibration amplitude sampled before, predicts a maximum value of the vibration amplitude at a next time interval from the sampled time series change of the maximum value of the vibration amplitude and the predicted amplitude curve, and outputs a warning signal to a warning unit when the predicted value reaches an upper limit value of an acceptable range of a preliminarily calculated maximum vibration amplitude.

17. A vibration monitoring method for monitoring vibration of a component of a jet pump to be monitored disposed in a reactor pressure vessel using an ultrasonic wave, comprising the steps of:
   reflecting the ultrasonic wave from an ultrasonic sensor attached to an outside of the reactor pressure vessel by a planar reflecting surface of a reflector mounted on a curved surface of the component of the jet pump to be monitored, and then receiving the ultrasonic wave by the ultrasonic sensor; and
   performing signal processing of the ultrasonic wave received by the ultrasonic sensor and measuring vibration displacement of the component of the jet pump to be monitored.

18. A vibration monitoring method for monitoring a position change based on wear and degradation due to vibration of a component of a jet pump to be monitored disposed in a reactor pressure vessel using an ultrasonic wave, comprising the steps of:

reflecting the ultrasonic wave from a plurality of ultrasonic sensors attached to an outside of the reactor pressure vessel along a longitudinal direction of the component of the jet pump to be monitored by the component of the jet pump to be monitored, and then receiving the ultrasonic wave by the ultrasonic sensors;

performing signal processing of the ultrasonic wave received by the ultrasonic sensors and measuring a position of the component of the jet pump to be monitored; and comparing a time series change of the position of the component of the jet pump to be monitored and position change data with development of wear of the component of the jet pump to be monitored, and predicting timing when the component of the jet pump to be monitored reaches an acceptable wear amount, wherein the position of the component of the jet pump to be monitored changes based on wear and degradation due to vibration of the component of the jet pump to be monitored.

19. A vibration monitoring method for monitoring vibration of a component of a jet pump to be monitored disposed in a reactor pressure vessel using an ultrasonic wave, comprising the steps of:

reflecting the ultrasonic wave from a plurality of ultrasonic sensors attached to an outside of the reactor pressure vessel along a longitudinal direction of the component of the jet pump to be monitored by a planar reflecting surface of a reflector mounted on a curved surface of the component of the jet pump to be monitored, and then receiving the ultrasonic wave by the ultrasonic sensors;

performing signal processing of the ultrasonic wave received by the ultrasonic sensors and measuring a vibration amplitude of the component of the jet pump to be monitored;

calculating a vibration frequency at which the vibration amplitude of the component of the jet pump to be monitored is a maximum and a maximum amplitude from the time series change of the vibration amplitude of the component of the jet pump to be monitored; and issuing a warning when the time series change of the vibration frequency at which the vibration amplitude of the component of the jet pump to be monitored is maximum reaches an acceptable limit value of a preliminarily calculated frequency change.

20. A vibration monitoring method for monitoring vibration of a component of a jet pump to be monitored disposed in a reactor pressure vessel using an ultrasonic wave, comprising the steps of:

reflecting the ultrasonic wave from a plurality of ultrasonic sensors attached to an outside of the reactor pressure vessel along a longitudinal direction of the component of the jet pump to be monitored by a planar reflecting surface of a reflector mounted on a curved surface of the component of the jet pump to be monitored, and then receiving the ultrasonic wave by the ultrasonic sensors;

performing signal processing of the ultrasonic wave received by the ultrasonic sensors and measuring a vibration amplitude of the component of the jet pump to be monitored;

calculating a vibration frequency at which the vibration amplitude of the component of the jet pump to be monitored is a maximum and a maximum amplitude from the time series change of the vibration amplitude of the component of the jet pump to be monitored; and issuing a warning when the time series change of a maximum value of the vibration amplitude of the component of the jet pump to be monitored reaches an upper limit value of an acceptable range of a preliminarily calculated maximum value of the vibration amplitude.

* * * * *